US008957043B2

(12) United States Patent
Leveillard et al.

(10) Patent No.: US 8,957,043 B2
(45) Date of Patent: *Feb. 17, 2015

(54) METHODS OF TREATING RETINITIS PIGMENTOSA USING NUCLEIC ACIDS ENCODING RDCVF1 OR RDCVF2

(71) Applicants: Novartis AG, Basel (CH); Universite de Strasbourg, Strasbourg (FR)

(72) Inventors: Thierry Leveillard, Maisons Alfort (FR); Jose Alain Sahel, Paris (FR); Saddek Mohand-Said, Paris (FR); David Hicks, Strasbourg (FR)

(73) Assignees: Novartis AG, Basel (CH); Universite de Strasbourg, Strasbourg (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/909,764

(22) Filed: Jun. 4, 2013

(65) Prior Publication Data

US 2013/0287738 A1 Oct. 31, 2013

Related U.S. Application Data

(60) Division of application No. 13/348,435, filed on Jan. 11, 2012, now Pat. No. 8,518,695, which is a continuation of application No. 11/739,739, filed on Apr. 25, 2007, now Pat. No. 8,114,849, which is a division of application No. 10/473,008, filed as application No. PCT/EP02/03810 on Apr. 5, 2002, now Pat. No. 7,795,387.

(30) Foreign Application Priority Data

Apr. 6, 2001 (FR) .................................... 01 04712

(51) Int. Cl.
*C12N 15/11* (2006.01)
*C12N 15/12* (2006.01)
*A61K 48/00* (2006.01)
*C12N 15/63* (2006.01)

(52) U.S. Cl.
USPC ........ 514/44 R; 435/455; 435/69.1; 514/20.8; 530/350

(58) Field of Classification Search
CPC ............. C12N 48/005; C12N 15/0621; C12N 2830/85; A61K 48/005
See application file for complete search history.

(56) References Cited

U.S. PATENT DOCUMENTS

| 4,771,036 | A | 9/1988 | Pigiet et al. |
| 6,106,825 | A | 8/2000 | Moyer et al. |
| 6,716,835 | B1 | 4/2004 | Picaud et al. |
| 8,071,745 | B2 | 12/2011 | Leveillard et al. |
| 8,114,849 | B2 * | 2/2012 | Leveillard et al. ......... 514/44 R |
| 8,394,756 | B2 * | 3/2013 | Leveillard et al. ............. 514/1 |
| 8,518,695 | B2 | 8/2013 | Leveillard et al. |
| 8,779,093 | B2 | 7/2014 | Leveillard et al. |
| 2006/0275794 | A1 | 12/2006 | Carrino et al. |
| 2012/0108523 | A1 | 5/2012 | Leveillard et al. |
| 2012/0108657 | A1 | 5/2012 | Leveillard et al. |
| 2013/0287738 | A1 | 10/2013 | Leveillard et al. |

FOREIGN PATENT DOCUMENTS

| EP | 1033405 | A3 | 9/2000 |
| FR | 2784030 | A1 | 4/2000 |
| FR | 2784898 | A1 | 4/2000 |
| WO | 98/32863 | A2 | 7/1998 |
| WO | 00/24359 | A2 | 5/2000 |
| WO | 01/53312 | A1 | 7/2001 |

OTHER PUBLICATIONS

Singh et al, Barriers for retinal gene therapy:Separating fact from fiction, Vision Research, (48) 2008, pp. 1671-1680.*
Acland, Gregory M. et al., "Gene therapy restores vision in a canine model of childhood blindness," Nature Genetics, vol. 28:92-95 (2001).
Borrás, Teresa, "Recent developments in ocular gene therapy," Experimental Eye Research, vol. 76:643-652 (2003).
Bowie, James U. et al., "Deciphering the Message in Protein Sequences: Tolerance to Amino Acid Substitutions," Science, vol. 247:1306-1310 (1990).
Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111:2129-2138 (1990).
Chapple, J. Paul et al., "Unfolding retinal dystrophies: a role for molecular chaperones?" Trends in Molecular Medicine, vol. 7(9):414-421 (2001).
Check, Erika, "Cancer fears cast doubts on future of gene therapy," Nature, vol. 421:678 (2003).
Das, Kumuda C. et al., "Thioredoxin, a Singlet Oxygen Quencher and Hydroxyl Radical Scavenger: Redox Independent Functions," Biochemical and Biophysical Research Communications, vol. 277:443-447 (2000).

(Continued)

*Primary Examiner* — Maria Marvich
(74) *Attorney, Agent, or Firm* — Nelson Mullins Riley & Scarborough LLP; Jane E. Remillard, Esq.; Jill Gorny Sloper, Esq.

(57) ABSTRACT

Disclosed are methods and compositions for early diagnosis, monitoring and treatment of retinal dystrophy, age-related macular degeneration, Bardet-Biedel syndrome, Bassen-kornzweig syndrome, best disease, choroidema, gyrate atrophy, congenital amourosis, refsun syndrome, stargardt disease and Usher syndrome. In particular, the invention relates to a protein, termed "Rdcvf1," that is differentially transcribed and expressed in subjects suffering from retinal dystrophies and the like, such as retinal dystrophy and age-related macular degeneration compared with nonsufferers, antibodies which recognize this protein, and methods for diagnosing such conditions.

15 Claims, 15 Drawing Sheets

(56) References Cited

OTHER PUBLICATIONS

El Sanharawi, M. et al., "Protein delivery for retinal diseases: From basic considerations to clinical applications," Progress in Retinal and Eye Research, vol. 29:443-465 (2010).
Frasson, Maria et al., "Glial Cell Line-Derived Neurotrophic Factor Induces Histologic and Functional Protection of Rod Photoreceptors in the rd/rd Mouse," Investigative Ophthalmology & Visual Science, vol. 40(11):2724-2734 (1999).
GenBank AC AC073678, DOE Joint Genome Institute, "Sequencing of Mouse," Jun. 29, 2000.
GenBank AC AC073700, DOE Joint Genome Institute, "Sequencing of Mouse," (2000).
GenBank AC AI716631, Soares, M.B., "UI-R-Y0-acc-d-07-0-UI.s1 UI-R-Y0 Rattus norvegicus C DNA clone UI-R-Y0-acc-d-07-0-UI 3-, mRNA sequence," (1999).
GenBank AC AK015847, Carninci, P. et al., "High-efficiency full-length cDNA cloning," Meth. Enzymol., vol. 303:19-44 (1999).
GenBank AC BC014127, Strausberg, R.L. et al., "Generation and initial analysis of more then 15,000 full-length human and mouse cDNA sequence," Proc. Natl. Acad. Sci. USA, vol. 99(26):16899-16903 (2002).
GenBank AC BC016199, Strausberg, R.L. et al., "Generation and initial analysis of more than 15,000 full-length human and mouse cDNA sequences," Proc. Natl. Acad. Sci. USA, vol. 99(26):16899-16903 (2002).
GenBank AC BC021911, Strausberg, R.L. et al., "Generation and initial analysis of more than 15,000 full-length human and mouse cDNA sequences," Proc. Natl. Acad. Sci. U.S.A., vol. 99(26):16899-16903 (2002) Sep. 11, 2007.
GenBank AC BC022521, Strausberg, R.L. et al., "Generation and initial analysis of more than 15,000 full-length human and mouse cDNA sequences," Proc. Natl. Acad. Sci. USA, vol. 99(26):16899-16903 (2002).
GenBank AC BC014027, Strausberg, R.L. et al., "Generation and initial analysis of more than 15,000 full-length human and mouse cDNA sequences," Proc. Natl. Acad. Sci. USA, vol. 99(26):16899-16903 (2002) Sep. 16, 2003.
GenBank AC BI731629, NIH-MGC http://mgc.nci.nih.gov/, "National Institute of Health, Mammalian Gene Collection (MGC)," (2001).
GenBank AC BI734135, NIH-MGC http://mgc.nci.nih.gov/, "National Institutes of Health, Mammalian Gene Collection (MGC)," (2001).
GenBank AC BI738445, NIH-MGC http://mgc.nci.nih.gov/, "National Institutes of Health, Mammalian Gene Collection (MGC)," (2001).
GenBank AC BG294111, Feb. 23, 2001.
GenBank AC Q8VC33, Gerhard, D.S. et al., "The status, quality, and expansion of the NIH full-length cDNA project: the Mammalian Gene Collection (MGC)," Genome Res., vol. 14(10B):2121-2127 (2004).
Hicks, David et al., "The Implications of Rod-Dependent Cone Survival for Basic and Clinical Research," Investigative Ophthalmology & Visual Science, vol. 40(13):3071-3074 (1999).
InterPro: IPR011594 Thioredoxin-like, retrieved online at http://www.ebi.ac.uk/interpro/IEntry?ac=IPR011594 (2008).
Kahle, PHilipp J. et al., "The emerging utility of animal models of chronic neurodegenerative diseases," Emerging Therapeutic Targets, vol. 5(1):125-132 (2001).
Lazic, Stanley E. et al., "Cell-based therapies for disorders of the CNS," Expert Opinion Ther. Patents, vol. 15 (10):1361-1376 (2005).
Makino, Yuichi et al., "Thioredoxin: a Redox-regulating Cellular Cofactor for Glucocorticoid Hormone Factor, Cross Talk between Endocrine Control of Stress Response and Cellular Antioxidant Defense System," J. Clin. Invest., vol. 98 (11):2469-2477 (1996).
Mohand-Said, Saddek et al., "Normal retina releases a diffusible factor stimulating cone survival in the retinal degeneration mouse," Proc. Natl. Acad. Sci. USA, vol. 95:8357-8362 (1998).
Mohand-Said, Saddek et al., "Rod-Cone Interactions: Developmental and Clinical Significance," Progress in Retinal and Eye Research, vol. 20(4):451-467 (2001).
Ohira, Akihiro et al., "Oxidative Stress Induces Adult T Cell Leukemia Derived Factor/Thioredoxin in the Rat Retina," Laboratory Investigation, vol. 70(2):279-285 (1994).
Opalinska, Joanna B. et al., "Nucleic-acid therapeutics: Basic Principles and Recent Applications," Nature Reviews, Drug Discovery, vol. 1:503-514 (2002).
Pawson, Tony et al., "Assembly of Cell Regulatory Systems Through Protein Interaction Domains," Science, vol. 300:445-452 (2003).
RetNet:Disease Table, "Genes and Mapped Loci Causing Retinal Diseases," retrieved online at http://www.sph.uth.tmc.edu/Retnet/disease.htm (2007)
Ritter, T. et al., "Is ex vivo adenovirus mediated gene transfer a therapeutic option for the treatment of corneal diseases?" Br. J. Ophthalmol., vol. 89:649-649 (2005).
Russell, S.J., "Replicating Vectors for Gene Therapy of Cancer: Risks, Limitations and Prospects," European Journal of Cancer, col. 30A(8):1165-1171 (1994).
Scullica, Luigi et al., "Diagnosis and classification of macular degenerations: an approach based on retinal function testing," Documenta Ophthalmologica, vol. 102:237-250 (2001).
Shibuki, Hiroto et al., "Protective Effect of Adult T-Cell Leukemia-Derived Factor on Retinal Ischemia-Reperfusion Injury in the Rat," Invest. Ophthalmol. Vis. Sci., vol. 39:1470-1477 (1998).
Sullivan, Lori S. et al., "Inherited retinal degeneration: exceptional genetic and clinical heterogeneity," Molecular Medicine Today, vol. 2(9):380-386 (1996).
Torchilin, Vladimir P. et al., "Peptide and protein drug delivery to and into tumors: challenges and solutions," DDT, vol. 8(6):259-266 (2003).
Verma, Inder M. et al., "Gene therapy—promises, problems and prospects," Nature, vol. 389:239-242 (1997).

\* cited by examiner

Figure 1:

Mouse RdCVF1 cDNA: SEQ ID NO:1

```
  1 ATCGGATCCCTCTCTGGGTCCCCAGCTCCTTGCATACTGCTACCATGGCA  50
 51 TCTCTCTTCTCTGGACGCATCTTGATCAGGAACAACAGCGACCAGGATGA 100
101 AGTGGAGACAGAGGCAGAGCTGAGCCGTAGGTTAGAGAATCGTCTGGTGT 150
151 TGCTGTTCTTCGGCGCCGGCGCCTGTCCCCAGTGCCAGGCCTTTGCCCCA 200
201 GTCCTCAAAGACTTCTTCGTGCGGCTCACTGACGAGTTCTACGTGCTGCG 250
251 GGCAGCACAGCTGGCCCTGGTCTATGTGTCCCAGGACCCTACAGAGGAGC 300
301 AACAGGACCTCTTCCTCAGGGACATGCCTGAAAAATGGCTCTTCCTGCCG 350
351 TTCCATGATGAACTGAGGAGGTGAGGCCCCAGGGAAGACCAGGGAGGGCT 400
401 TCCTGGAGAAGGCATTTCCCTGGAGGTTTACTGTCCTGGTACTACTTGTG 450
451 CATAAAGAGGTATTCCTC 468
```

Polypeptide : ATG to TGA: SEQ ID NO:2

```
  1 MASLFSGRIL IRNNSDQDEV ETEAELSRRL ENRLVLLFFG AGACPQCQAF
 51 APVLKDFFVR LTDEFYVLRA AQLALVYVSQ DPTEEQQDLF LRDMPEKWLF
101 LPFHDELRR
```

Figure 2:

Mouse RdCVF1L cDNA: SEQ ID NO:3

```
  1 CCCCAGCTCC TTGCATACTG CTACCATGGC ATCTCTCTTC TCTGGACGCA
 51 TCTTGATCAG GAACAACAGC GACCAGGATG AAGTGGAGAC AGAGGCAGAG
101 CTGAGCCGTA GGTTAGAGAA TCGTCTGGTG TTGCTGTTCT TCGGCGCCGG
151 CGCCTGTCCC CAGTGCCAGG CCTTTGCCCC AGTCCTCAAA GACTTCTTCG
201 TGCGGCTCAC TGACGAGTTC TACGTGCTGC GGGCAGCACA GCTGGCCCTG
251 GTCTATGTGT CCCAGGACCC TACAGAGGAG CAACAGGACC TCTTCCTCAG
301 GGACATGCCT GAAAAATGGC TCTTCCTGCC GTTCCATGAT GAACTGAGGA
351 GGGACCTCGG GCGCCAGTTC TCTGTCCGTC AACTGCCAGC GGTTGTGGTA
401 CTTAAGCCTG GTGGGACGT GCTGACAAGC GACGCCACGG AGGAGATCCA
451 GCGTCTGGGA CCCGCCTGCT TTGCCAACTG GCAGGAGGCC GCAGAGCTCC
501 TGGACCGCAG CTTCCTGCAA CCGGAGGATT TGGATGAGCC TGCGCGGCGC
551 AGCATCACCG AGCCTCTGCG CCGTCGCAAG TACCGAGTAG ACCGGGATGT
601 CGGCGGGAGC GGGGCGAAAC GGCGCGACTC TGGTGAACCC CAGGGGGACG
651 CGGGTACAAG GCGGAGCTC TGGTGACTCC CAGGGTAGGA GTGGGGACCG
701 GAGCTCTGGT GACACCAAAG TACCGGTGCA CGACCGAGGT TGATGACCCT
751 CCCGAAGGAA CCGG
```

Polypeptide : ATG to TGA: SEQ ID NO:4

```
  1 MASLFSGRIL IRNNSDQDEV ETEAELSRRL ENRLVLLFFG AGACPQCQAF
 51 APVLKDFFVR LTDEFYVLRA AQLALVYVSQ DPTEEQQDLF LRDMPEKWLF
101 LPFHDELRRD LGRQFSVRQL PAVVVLKPGG DVLTSDATEE IQRLGPACFA
151 NWQEAAELLD RSFLQPEDLD EPARRSITEP LRRRKYRVDR DVGGSGAKRR
201 DSGEPQGDAG TRAELW
```

Figure 3:

Human RdCVF1 cDNA: SEQ ID NO:5

```
  1  CCCAGCACCC AACCCAGGTT ACCATGGCCT CCCTGTTCTC TGGCCGCATC
 51  CTGATCCGCA ACAATAGCGA CCAGGACGAG CTGGATACGG AGGCTGAGGT
101  CAGTCGCAGG CTGGAGAACC GGCTGGTGCT GCTGTTCTTT GGTGCTGGGG
151  CTTGTCCACA GTGCCAGGCC TTCGTGCCCA TCCTCAAGGA CTTCTTCGTG
201  CGGCTCACAG ATGAGTTCTA TGTACTGCGG GCGGCTCAGC TGGCCCTGGT
251  GTACGTGTCC CAGGACTCCA CGGAGGAGCA GCAGGACCTG TTCCTCAAGG
301  ACATGCCAAA GAAATGGCTT TTCCTGCCCT TTGAGGATGA TCTGAGGAGG
351  TGA
```

Polypeptide : ATG to TGA: SEQ ID NO:6

```
  1  MASLFSGRIL IRNNSDQDEL DTEAEVSRRL ENRLVLLFFG AGACPQCQAF
 51  VPILKDFFVR LTDEFYVLRA AQLALVYVSQ DSTEEQQDLF LKDMPKKWLF
101  LPFEDDLRR
```

Figure 4:

Human RdCVF1L cDNA: SEQ ID NO:7

```
  1  CCGGGGACCA CACGCCGCGC TGTCCCCAGC ACCCAACCCA GGTTACCATG
 51  GCCTCCCTGT TCTCTGGCCG CATCCTGATC CGCAACAATA GCGACCAGGA
101  CGAGCTGGAT ACGGAGGCTG AGGTCAGTCG CAGGCTGGAG AACCGGCTGG
151  TGCTGCTGTT CTTTGGTGCT GGGGCTTGTC CACAGTGCCA GGCCTTCGTG
201  CCCATCCTCA AGGACTTCTT CGTGCGGCTC ACAGATGAGT TCTATGTACT
251  GCGGGCGGCT CAGCTGGCCC TGGTGTACGT GTCCCAGGAC TCCACGGAGG
301  AGCAGCAGGA CCTGTTCCTC AAGGACATGC CAAAGAAATG GCTTTTCCTG
351  CCCTTTGAGG ATGATCTGAG GAGGGACCTC GGGCGCCAGT TCTCAGTGGA
401  GCGCCTGCCG GCGGTCGTGG TGCTCAAGCC GGACGGGGAC GTGCTCACTC
451  GCGACGGCGC CGACGAGATC CAGCGCCTGG GCACCGCCTG CTTCGCCAAC
501  TGGCAGGAGG CGGCCGAGGT GCTGGACCGC AACTTCCAGC TGCCAGAGGA
551  CCTGGAGGAC CAGGAGCCAC GGAGCCTCAC CGAGTGCCTG CGCCGCCACA
601  AGTACCGCGT GGAAAAGGCG GCGCGAGGCG GGCGCGACCC CGGGGGAGGG
651  GGTGGGGAGG AGGGCGGGGC CGGGGGGCTG TTCTGA
```

Polypeptide : ATG to TGA: SEQ ID NO:8

```
  1  MASLFSGRIL IRNNSDQDEL DTEAEVSRRL ENRLVLLFFG AGACPQCQAF
 51  VPILKDFFVR LTDEFYVLRA AQLALVYVSQ DSTEEQQDLF LKDMPKKWLF
101  LPFEDDLRRD LGRQFSVERL PAVVVLKPDG DVLTRDGADE IQRLGTACFA
151  NWQEAAEVLD RNFQLPEDLE DQEPRSLTEC LRRHKYRVEK AARGGRDPGG
201  GGGEEGGAGG LF
```

Figure 5:

Mouse RdCVF2 cDNA: SEQ ID NO:9

```
  1 ATAAAATAGA GGGTGGGAGA GGTTGATGGC GTGGCTCTGC TTTTTGGTGC
 51 GGGGCACCCA GCTGTCATCG CTGCTGTCGC AGCTTCTGGA GTGGCCACTG

101 TGCTCTCTCC TCCCTTCGGC TCAAGGTGAG CTGTTCCAGC AGAAGGCGGG
151 GCTGAGAGGC GCCTAGTGCT GCGGGAGGCT CAGTGTCATC TTCCAGCTAA
201 CAGGTGGCCG TGCAGCCCAG GGCTCGTCTC TCCACTGTGT CCTCTTCACG
251 CCGAGCTCGT GGCGATGGTG GACGTGCTGG GCGGGCGGCG CCTGGTGACC
301 CGGGAGGGCA CGGTGGTGGA GGCCGAGGTG GCGCTGCAGA ACAAGGTGGT
351 AGCTTTGTAC TTTGCGGCGG GCCGGTGCTC GCCCAGCCGC GACTTCACGC
401 CGCTGCTCTG CGACTTCTAC ACGGAGCTGG TGAGCGAGGC GCGGCGGCCC
451 GCTCCCTTCG AGGTGGTTTT CGTGTCGGCA GACGGCAGTG CGGAGGAGAT
501 GTTGGACTTC ATGCGCGAGC TGCACGGCTC CTGGCTGGCA TTGCCCTTCC
551 ACGACCCCTA CCGGCAGTGA GTGGGACCC AGGGGTCATG GGGCTGGCGC
```

Polypeptide : ATG to TGA: SEQ ID NO:10

```
  1 MVDVLGGRRL VTREGTVVEA EVALQNKVVA LYFAAGRCSP SRDFTPLLCD
 51 FYTELVSEAR RPAPFEVVFV SADGSAEEML DFMRELHGSW LALPFHDPYR
101 Q
```

Figure 6:

Mouse RdCVF2L cDNA: SEQ ID NO:11

```
   1 TTGACTCTGG TGGGTAGAGA GGGTTTGCAA GGCAGGATAA AATAGAGGGT
  51 GGGAGAGGTT GATGGCGTGG CTCTGCTTTT TGGTGCGGGG CACCAGCTGT
 101 CATCGCTGCT GTCGCAGCTT CTGGAGTGGC CACTGTGCTC TCTCCTCCCT
 151 TCGGCTCAAG GTGAGCTGTT CCAGCAGAAG GCGGGGCTGA GAGGCGCCTA
 201 GTGCTGCGGG AGGCTCAGTG TCATCTTCCA GCTAACAGGT GGCCGTGCAG
 251 CCCAGGGCTC GTCTCTCCAC TGTGTCCTCT TCACGCCGAG CTCGTGGCGA
 301 TGGTGGACGT GCTGGGCGGG CGGCGCCTGG TGACCCGGGA GGGCACGGTG
 351 GTGGAGGCCG AGGTGGCGCT GCAGAACAAG GTGGTAGCTT TGTACTTTGC
 401 GGCGGGCCGG TGCTCGCCCA GCCGCGACTT CACGCCGCTG CTCTGCGACT
 451 TCTACACGGA GCTGGTGAGC GAGGCGCGGC GGCCCGCTCC CTTCGAGGTG
 501 GTTTTCGTGT CGGCAGACGG CAGTGCGGAG GATGTTGGAC TTCATGCGC
 551 CGAGCTGCAC GGCTCCTGGC TGGCATTGCC CTTCCACGAC CCCTACCGGC
 601 ATGAACTGAA GAAGAGGTAC GAAATCACCG CCATCCCCAA GCTGGTGGTC
 651 ATCAAGCAGA ACGGAGCTGT CATCACCAAC AAAGGGCGGA AGCAGATCCG
 701 AGAGCGCGGG CTAGCTTGCT TTCAGAACTG GGTGGAAGCA GCCGATGTTT
 751 TCCAAAACTT CTCGGGGTGA CCAGGGCAGT TGCTGGAAGT TCAGGGCAAC
 801 TATCTTCAAA AAGGGCTTAG CTGGTTCCCT TCTCTGCTGA GGAATGTCAT
 851 TGTAGAGTCA CCATGCTGTG ACAGAGAGCA TAAACTGCTC AGGAAAGAAC
 901 TACGTCTGCC CCCTGTGGGT CCTAGAGCTC CGTTGAATGT TTATTTCTTA
 951 CACCTTTCTC CACCGGTGCC TAGGATCCAG GACACATCAG CCACGAGTTA
1001 ACAGAACTCT ATGCAAGATG CTCTTTCCTA CAGGAAATTT CTTTGATAAA
1051 TTGACCTATG GAGGTGATAC ATTTTCTGAT GACATTTTTG TGATGCTTTG
1101 GTAAACGTAT TTATTACTCG GGTTTGTAGA CTGTGTAATT TAATAAACCA
1151 ACACTCACAC TTTG
```

Polypeptide : ATG to TGA: SEQ ID NO:12

```
  1 MVDVLGGRRL VTREGTVVEA EVALQNKVVA LYFAAGRCSP SRDFTPLLCD
```

Figure 6: (continued)

```
 51 FYTELVSEAR RPAPFEVVFV SADGSAEEML DFMRELHGSW LALPFHDPYR
101 HELKKRYEIT AIPKLVVIKQ NGAVITNKGR KQIRERGLAC FQNWVEAADV
151 FQNFSG
```

Figure 7:

Human RdCVF2 cDNA: SEQ ID NO:13

```
   1 GTGTGGGCGG GGCGCAGTTG GGGGAGGGTG CAGAGACCTG AGGGCTTGAG
  51 GTTGCCTGGC TGGCCCCGCT CCCAGAGGCG GGTGCCGCGC TGTCGCCCAG
 101 GTATCTGGGG TCTCTGGTGT CTGAGTGTCT CATTGTCGGC GCGAACACAA
 151 TTGCTCCAGC CACAGGCGAG GCCTGGCCAA GGTGTGGGCG CATCTAGGGC
 201 AGGTCTTGAG AGGTCCAGCG CCCGGTGGTG CGGACAGAGG CGGGGCACCG
 251 CGGCGCTCGC CGCCGCCTCC CCGCAGGTGA TCATCCTCCT GCAGGTGTCC
 301 TCGGGTCTCA GGTGGCTGCG TGTCTGCGCC ATGGTTGACA TTCTGGGCGA
 351 GCGGCACCTG GTGACCTGTA AGGGCGCGAC GGTGGAGGCC GAGGCGGCGC
 401 TGCAGAACAA GGTGGTGGCA CTGTACTTCG CGGCGGCCCG GTGCGCGCCG
 451 AGCCGCGACT TCACGCCGCT GCTCTGCGAC TTCTATACGG CGCTGGTGGC
 501 CGAGGCGCGG CGGCCCGCGC CCTTCGAAGT GGTCTTCGTG TCAGCCGACG
 551 GCAGCTGCCA GGAGATGCTG GACTTCATGC GCGAGCTGCA TGGCGCCTGG
 601 CTGGCGCTGC CCTTCCACGA CCCCTACCGG CAACGGAGTC TCGCTCTGTT
 651 GCCCAGGCTG GAGTGCAGTG GCGTGATCTT AGCTCACTGC AACCTTTGCC
 701 TCCTGGGTTC AAGTGATTCT CTAGCCTTAG CCTCCTGAGC ATCTGGGACT
 751 ACAGCCATTG CTGTGAATTA CGTGAGGGAA AGATATTGAA GAGGAGTTGG
 801 ACACTCCGAG AGTGCAGCTG TTCTCCCCCC GCACCATCCG TGTCCTGCAT
 851 TCTGCGAGTC TGTGCTCATT AACAATGTGC TGTGACCATG TGACTCAGCA
 901 ATCCTGCTGC TGGGTATATA CCCGAAAGAA AGGAAAAGGA AGCCAGTATA
 951 TTGAAGAGGT ATCTGCACCC CCATGTTTAT TGCAGCACTG TTCACAACAG
1001 CCAAGATTTG GAAGCAACCT AAGTGTCCAT CAACAGATGA ATGGATAAAG
1051 AAAACGTGGT ACATATACAC AATGGAGTAC TCTTCAGCCA TTAAAAAAAT
1101 GAGATTCTGT CATTTGCAAT AATATAGATG GAAAAGGAGG CCCTTATGTG
1151 AAGTGAAATA AGCCAGGCAC AGAAAGACAA ACATCACATG TTCTCACTTA
1201 TTTGTGGGAT CTAATGATCA AAACAATTGA ACTCTTGGAC ATAGAGAGTA
1251 GAAGGTTGGT TACCAGAAGC TGGAAAGGAA AGTGGGGTTG GGAGGAAGGT
1301 GGGAATGGTT AATAGGTACA AAAAAATACA AAGAATAAAT AAGACCTAAT
1351 ATTTGATAGC ACAACAGTGT GACTACTGTC AATAATCATT TAATTGTACA
1401 TTTAAAAATA ACTATAATTG CATTGTTTGT AACACAAAAG ATAAATGCTT
1451 GAGGAGAAAA AAAAAAAAA AA
```

Polypeptide : ATG to TGA : SEQ ID NO:14

```
   1 MVDILGERHL VTCKGATVEA EAALQNKVVA LYFAAARCAP SRDFTPLLCD
  51 FYTALVAEAR RPAPFEVVFV SADGSCQEML DFMRELHGAW LALPFHDPYR
 101 QRSLALLPRL ECSGVILAHC NLCLLGSSDS LALAS
```

Figure 8:

Pileup short sequences :

```
                                 1                                                        50
SEQ ID NO:  2   mRdCVF1  MASLFSGRIL IRNNSDQDEV ETEAELSRRL ENRLVLLFFG AGACPQCQAF
SEQ ID NO:  6   hRdCVF1  MASLFSGRIL IRNNSDQDEL DTEAEVSRRL ENRLVLLFFG AGACPQCQAF
SEQ ID NO: 10   mRdCVF2  MVDVLGGRRL VTREG....T VVEAEVA..L QNKVVALYFA AGRCSPSRDF
```

Figure 8: (continued)

```
SEQ ID NO: 14    hRdCVF2   MVDILGERHL VTCKG....A TVEAEAA..L QNKVVALYFA AARCAPSRDF 51                                                     100
                 mRdCVF1   APVLKDFFVR LTDEFYVLRA AQLALVYVSQ DPTEEQQDLF LRDMPEKWLF
                 hRdCVF1   VPILKDFFVR LTDEFYVLRA AQLALVYVSQ DSTEEQQDLF LKDMPKKWLF
                 mRdCVF2   TPLLCDFYTE LVSE..ARRP APFEVVFVSA DGSAEEMLDF MRELHGSWLA
                 hRdCVF2   TPLLCDFYTA LVAE..ARRP APFEVVFVSA DGSCQEMLDF MRELHGAWLA 101                                   143
                 mRdCVF1   LPFHDELRR
                 hRdCVF1   LPFEDDLRR
                 mRdCVF2   LPFHDPYRQ
                 hRdCVF2   LPFHDPYRQR SLALLPRLEC SGVILAHCNL CLLGSSDSLA LAS
```

Pileup long sequences :

```
                           1                                                      50
SEQ ID NO: 4     mRdCVF1L  MASLFSGRIL IRNNSDQDEV ETEAELSRRL ENRLVLLFFG AGACPQCQAF
SEQ ID NO: 8     hRdCVF1L  MASLFSGRIL IRNNSDQDEL DTEAEVSRRL ENRLVLLFFG AGACPQCQAF
SEQ ID NO: 12    mRdCVF2L  MVDVLGGRRL VTREG....T VVEAEVA..L QNKVVALYFA AGRCSPSRDF
SEQ ID NO: 14    hRdCVF2   MVDILGERHL VTCKG....A TVEAEAA..L QNKVVALYFA AARCAPSRDF 51                                                     100
                 mRdCVF1L  APVLKDFFVR LTDEFYVLRA AQLALVYVSQ DPTEEQQDLF LRDMPEKWLF
                 hRdCVF1L  VPILKDFFVR LTDEFYVLRA AQLALVYVSQ DSTEEQQDLF LKDMPKKWLF
                 mRdCVF2L  TPLLCDFYTE LVSE..ARRP APFEVVFVSA DGSAEEMLDF MRELHGSWLA
                  hRdCVF2  TPLLCDFYTA LVAE..ARRP APFEVVFVSA DGSCQEMLDF MRELHGAWLA 101                                                    150
                 mRdCVF1L  LPFHDELRRD ...LGRQFSV RQLPAVVVLK PGGDVLTSDA TEEIQRLGPA
                 hRdCVF1L  LPFEDDLRRD ...LGRQFSV ERLPAVVVLK PDGDVLTRDG ADEIQRLGTA
                 mRdCVF2L  LPFHDPYRHE ...LKKRYEI TAIPKLVVIK QNGAVITNKG RKQIRERGLA
                  hRdCVF2  LPFHDPYRQR SLALLPRLEC SGV...ILAH CNLCLLGSSD SLALAS 151                                                    200
                 mRdCVF1L  CFANWQEAAE LLDRSFLQPE DLDEPARRSI TEPLRRRKYR VDRDVGGSGA
                 hRdCVF1L  CFANWQEAAE VLDRNFQLPE DLEDQEPRSL TECLRRHKYR VEKAARGG..
                 mRdCVF2L  CFQNWVEAAD VFQNFSG
                  hRdCVF2

201            219
                 mRdCVF1L  KRRDSGEPQG DAGTRAELW
                 hRdCVF1L  ..RDPGGGGG EEGGAGGLF
                 mRdCVF2L
                  hRdCVF2
```

Figure 9:

SEQ ID NO: 26: 5' cgggatccATGGCATCTCTCTTCTCTGGACGC 3'

SEQ ID NO: 27: 5' ggaattcTCACCTCCTCAGTTCATCATGGAA 3'

Figure 10:

```
                        1                                                    50
SEQ ID NO: 2   RdCVF1   MASLFSGRIL IRNNSDQDEV ETEAELSRRL ENRLVLLFFG AGACPQCQAF
SEQ ID NO: 10  RdCVF2   MVDVLGGRRL V....TREGT VVEAEVA..L QNKVVALYFA AGRCSPSRDF 51                                                   100
               RdCVF1   APVLKDFFVR LTDEFYVLRA AQLALVYVSQ DPTEEQQDLF LRDMPEKWLF
               RdCVF2   TPLLCDFYTE LVSE..ARRP APFEVVFVSA DGSAEEMLDF MRELHGSWLA

101
               RdCVF1   LPFHDELRR
               RdCVF2   LPFHDPYRQ
```

Figure 11:

```
bc016199              mouse RdCVF2   SEQ ID NO: 10
bg707818              human RdCVF2   SEQ ID NO: 36

1                                                     50
bc016199    MVDVLGGRRL VTREGTVVEA EVALQNKVVA LYFAAGRCSP SRDFTPLLCD
bg707818    MVDILGERHL VTCKGATVEA EAALQNKVVA LYFAAARCAP SRDFTPLLCD 51                                                    100
bc016199    FYTELVSEAR RPAPFEVVFV SADGSAEEML DFMRELHGSW LALPFHDPYR
bg707818    FYTALVAEAR RPAPFEVVFV SADGSCQEML DFMRELHGAW LALPFHEPYR 101        120
bc016199    Q*
bg707818    QRSLALLPRL ECSGVILAH*
```

Figure 12:

```
Name: mRdCVF2       mouse sequence bc016199 SEQ ID NO: 37
Name: be552141      homo sapiens   SEQ ID NO: 20
Name: bi517442      homo sapiens   SEQ ID NO: 21
Name: bg707818      homo sapiens   SEQ ID NO: 22
Name: bi603812      homo sapiens   SEQ ID NO: 23 mRdCVF2                                                ATGGT GGACGTGCTG
be552141   TGTCCTCGGG TCTCAGGTGG CTGCGTGTCT GCGCCATGGT TGACATTCTG
bi517442   TGTCCTCGGG TCTCAGGTGG CTGCGTGTCT GCGCCATGGT TGACATTCTG
bg707818   TGTCCTCGGG TCTCAGGTGG CTGCGTGTCT GCGCCATGGT TGACATTCTG
bi603812   TGTCCTCGGG TCTCAGGTGG CTGCGTGTCT GCGCCATGGT TGACATTCTG mRdCVF2    GGCGGCGGC  GCCTGGTGAC CCGGGAGGGC ACGGTGGTGG AGGCCGAGGT
be552141   GGCGAGCGGC ACCTGGTGAC CTGTAAGGGC GCGACGGTGG AGGCCGAGGC
bi517442   GGCGAGCGGC ACCTGGTGAC CTGTAAGGGC GCGACGGTGG AGGCCGAGGC
bg707818   GGCGAGCGGC ACCTGGTGAC CTGTAAGGGC GCGACGGTGG AGGCCGAGGC
bi603812   GGCGAGCGGC ACCTGGTGAC CTGTAAGGGC GCGACGGTGG AGGCCGAGGC mRdCVF2    GGCGCTGCAG AACAAGGTGG TAGCTTTGTA CTTTGCGGCG GGCCGGTGCT
be552141   GGCGCTGCAG AACAAGGTGG TGGCACTGTA CTTCGCGGCG GCCCGGTGCG
bi517442   GGCGCTGCAG AACAAGGTGG TGGCACTGTA CTTCGCGGCG G.CCGGTGCG
bg707818   GGCGCTGCAG AACAAGGTGG TGGCACTGTA CTTCGCGGCG GCCCGGTGCG
bi603812   GGCGCTGCAG AACAAGGTGG TGGCACTGTA CTTCGCGGCG GCCCGGTGCG
```

Figure 12: (continued)

```
mRdCVF2   CGCCCAGCCG CGACTTCACG CCGCTGCTCT GCGACTTCTA CACGGAGCTG
be552141  CGCCGAGCCG CGACTTCACG CCGCTGCTCT GCGACTTCTA TACGGCGCTG
bi517442  CGCCGAGCCG CGA.TTCACG CCGCTGCTCT GCGACTTCTA TACGGCGCTG
bg707818  CGCCGAGCCG CGACTTCACG CCGCTGCTCT GCGACTTCTA TACGGCGCTG
bi603812  CGCCGAGCCG CGACTTCACG CCGCTGCTCT GCGACTTCTA TACGGCGCTG mRdCVF2   GTGAGCGAGG CGCGGCGGCC CGCTCCCTTC GAGGTGGTTT TCGTGTCGGC
be552141  GTGGCCGAGG CGCGGCGGCC CGCGCCCTTC GAAGTGGTCT TCGTGTCAGC
bi517442  GTGGCCGAG. ...CGCGGGG CCGCGCCTTC GAAGTGGTCT TCGTGTCAGC
bg707818  GTGGCCGAGG CGCGGCGGCC CGCGCCCTTC GAAGTGGTCT TCGTGTCAGC
bi603812  GTGGCCGAGG CGCGGCGGCC CGCGCCCTTC GAAGTGGTCT TCGTGTCAGC mRdCVF2   AGACGGCAGT GCGGAGGAGA TGT.TGGACT TCATGCGCGA GCTGCACGGC
be552141  CGACGGCAGC TCCCAGGAGA TGC.TGGACT TCATGCGCGA GCTGCATGGC
bi517442  CGACGGCAGC TCCCAGGAGA TGC.TGGACT TCATGCGCGA GCTG.ATGGC
bg707818  CGACGGCAGC TGCCAGGAGA TGC.TGGACT TCATGCGCGA GCTGCATGGC
bi603812  CGACGGCAGC TGCCAGGAGA TGCTTGGACT TCATGCGCGA GCTGCATTGC mRdCVF2   TCCTGGC.TG GCATTGCCCT TCCACGACCC CTACCGGCAG TGA
be552141  GCCTGGC.TG GCGCTGCCCT TCCACGACCC CTACCGGCAC CATTGCTGTG
bi517442  GCCTGGC.TG GCGCTG.CCT TCCACGACCC CTACCGGCAC AGCCGGAGCC
bg707818  GCCTGGC.TG GCGCTGCCCT TCCACGAACC CTACCGGCAA CGGAGTCTCG
bi603812  GCCTGGCTTG GCGCTGCCCT TCCACGACCC CTACCGGCAA CGGAGTCTCG
```

Figure 13:

pileup

```
                    GapWeight: 5
              GapLengthWeight: 1

Name: RdCVF1   SEQ ID NO: 38
  Name: bg299078 SEQ ID NO: 15
  Name: ai716631 SEQ ID NO: 16
  Name: bg294111 SEQ ID NO: 17
  Name: be108041 SEQ ID NO: 18Rev
  Name: bg395178 SEQ ID NO: 19

1                                                50
  RdCVF1    ~~~~~~~~~~ ~~~~~~~~~~ ~~~~~~~~~~ ~~~~~~~~~~ ~~~~~~~~~~
  bg299078  ~~~~~~~~~~ ~~~~~~~~~~ ~~~~~~~~~~ ~~~ATCGGATC CTCTCTGGGT
  ai716631  ~~~~~~~~~~ ~~~~~~~~~~ ~~~~~~~~~~ ~~~~~~~~CG GCCGCTTAAT SINE
  bg294111  ~~~~~~~~~~ ~~~~~~~~~~ ~~~~~~~~~~ ~~~~~~~~~~ ~~~~~~~~~~
  be108041  ACGAGGTCAA CCTTGGCTAC ACAGGGAGTC TGAGGACAGC ATGGGNTACA
  bg395178  ~~~~~~~~~~ ~~~~~~~~~~ ~~~~~~~~~~ ~~~~~~~~~A CGCCGCGCTG 51                                               100
  RdCVF1    ~~~~~~~~~~ ~~~~~~~~~~ ~~~~~ATGGC ATCTCTCTTC TCTGGACGCA
  bg299078  CCCCAGCTCC TTGCATACTG CTACCATGGC ATCTCTCTTC TCTGGACGCA
  ai716631  TAAGACGGAT CCCCGACTAC GTAGTCGGGA ATTCGGCACG AGGGGCCGCA
  bg294111  ~~~CAGCTCC TTGCATACTG CTACCATGGC ATCTCTCTTC TCTGGACGCA
  be108041  AGAAACCCTC TCTCAAAACC AAACAAGGCC TGGCAGTACT AGTGCACTTG
  bg395178  TCCCCAGCAC CCAACCCAGG TTACCATGGC CTCCCTGTTC TCTGGCCGCA 101                                              150
  RdCVF1    TCTTGATCAG GAACAACAGC GACCAGGATG AAGTGGAGAC AGAGGCAGAG
```

Figure 13: (continued)

```
bg299078   TCTTGATCAG GAACAACAGC GACCAGGATG AAGTGGAGAC AGAGGCAGAG
ai716631   TCTTGATCAG GAACAACAGC GACCAGGATG AAGTGGAGAC AGAGGCAGAG
bg294111   TCTTGATCAG GAACAACAGC GACCAGGATG AAGTGGAGAC AGAGGCAGAG
be108041   GGAGGCAGAG GAACAACAGC GACCAGGATG AAGTGGAGAC AGAGGCAGAG
bg395178   TCCTGATCCG CAACAATAGC GACCAGGACG AGCTGGATAC GGAGGCTGAG 151                                                200
RdCVF1     CTGAGCCGTA GGTTAGAGAA TCGTCTGGTG TTGCTGTTCT TCGGCGCCGG
bg299078   CTGAGCCGTA GGTTAGAGAA TCGTCTGGTG TTGCTGTTCT TCGGCGCCGG
ai716631   CTGAGCCGCC GGTTAGAGAA TCGTCTTGTG CTACTGTTCT TCGGTGCTGG
bg294111   CTGAGCCGTA GGTTAGAGAA TCGTCTGGTG .TGCTGTTCT TCGGCGCCGG
be108041   CTGAGCCGCC GGTTAGAGAA TCGTCTTGTG CTACTGTTCT TCGGTGCTGG
bg395178   GTCAGTCGCA GGCTGGAGAA CCGGCTGGTG CTGCTGTTCT TTGGTGCTGG 201                                                250
RdCVF1     CGCCTGTCCC CAGTGCCAGG CCTTTGCCCC AGTCCTCAAA GACTTCTTCG
bg299078   CGCCTGTCCC CAGTGCCAGG CC.TTGCCCC AGTCCTCAAA GACTTCTTCG
ai716631   GGCCTGTCCC CAGTGCCAGG CCTTCGCCCC AGTCCTCAAA GACTTCTTCG
bg294111   CGCCTGTCCC CAGTGCCAGG CC.TTGCCCC AGTCCTCAAA GACTTCTTCG
be108041   GGCCTGTCCC CAGTGCCAGG CCTTCGCCCC AGTCCTCAAA GACTTCTTCG
bg395178   GGCTTGTCCA CAGTGCCAGG CCTTCGTGCC CATCCTCAAG GACTTCTTCG 251                                                300
RdCVF1     TGCGGCTCAC TGACGAGTTC TACGTGCTGC GGGCAGCACA GCTGGCCCTG
bg299078   TGCGGCTCAC TGACGAGTTC TACGTGCTGC GGGCAGCACA GCTGGCCCTG
ai716631   TGCGGCTCAC TGATGAGTTC TACGTGCTAC GGGCAGCACA GCTGGCCCTG
bg294111   TGCGGCTCAC TGACGAGTTC TACGTGCTGC GGGCAGCACA GCTGGCCCTG
be108041   TGCGGCTCAC TGATGAGTTC TACGTGCTAC GGGCAGCACA GCTGGCCCTG
bg395178   TGCGGCTCAC AGATGAGTTC TATGTACTGC GGGCGGCTCA GCTGGCCCTG 301                                                350
RdCVF1     GTCTATGTGT CCCAGGACCC TACAGAGGAG CAACAGGACC TCTTCCTCAG
bg299078   GTCTATGTGT CCCAGGACCC TACAGAGGAG CAACAGGACC TCTTCCTCAG
ai716631   GTCTATGTGT CCCAGGACCC TACAGAGGAG CAACAGGACC TGTTCCTCCG
bg294111   GTCTATGTGT CCCAGGACCC TACAGAGGAG CAACAGGACC TCTTCCTCAG
be108041   GTCTATGTGT CCCAGGACCC TACAGAGGAG CAACAGGACC TGTTCCTCCG
bg395178   GTGTACGTGT CCCAGGACTC CACGGAGGAG CAGCAGGACC TGTTCCTCAA 351                                                400
RdCVF1     GGACATGCCT GAAAAATGGC TCTTCCTGCC GTTCCA.TGA TGAACTGAGG
bg299078   GGACATGCCT GAAAAATGGC TCTTCCTGCC GTCCCACTGA TGAACTGAGG
ai716631   GGACATGCCT GAAAAGTGGC TCTTCCTGCC GTTCCA.TGA TGACCTGAGG
bg294111   GGACATGCCT GAAAAATGGC TCTTCCTGCC GTTCCA.TGA TGAACTGAGG
be108041   GGACATGCCT GAAAAGTGGC TCTTCCTGCC GTTCCA.TGA TGACCTGAGG
bg395178   GGACATGCCA AAGAAATGGC TTTTCCTGCC CTTTGA.GGA TGATCTGAGG 401                                                450
RdCVF1     AGGTGA~~~~ ~~~~~~~~~~ ~~~~~~~~~~ ~~~~~~~~~~ ~~~~~~~~~~
bg299078   AGGTGAGGCC CCAGGGAAGA CCAGGGAGGG CTTCCTGGAG AAGGCATTTC
ai716631   AGAGACCTCG GGCGCCAGTT CTCCGT~~~~ ~~~~~~~~~~ ~~~~~~~~~~
bg294111   AGGGACCTCG GGCGCCAGTT CTCTGTCCGT CAACTGCCAG CGGTTGTGGT
be108041   AGTAATAAAA ATTAGAGGTT GTGGCTCAAA AAAAAAAAAA AAAA~~~~~~
bg395178   AGGGACCTCG GGCGCCAGTT CTCAGTGGAG CGCCTGCCGG CGGTCGTGGT 451                                                500
RdCVF1     ~~~~~~~~~~ ~~~~~~~~~~ ~~~~~~~~~~ ~~~~~~~~~~ ~~~~~~~~~~
bg299078   CCTGGAGGTT TACTGTCCTG GTACTACTTG TGCACTAAAG AGGTATTCCT
ai716631   ~~~~~~~~~~ ~~~~~~~~~~ ~~~~~~~~~~ ~~~~~~~~~~ ~~~~~~~~~~
bg294111   ACTTAAGCCT GGTGGGGACG TGCTGACAAG CGACGCCACG GAGGAGATCC
be108041   ~~~~~~~~~~ ~~~~~~~~~~ ~~~~~~~~~~ ~~~~~~~~~~ ~~~~~~~~~~
```

Figure 13: (continued)

```
bg395178   GCTCAAGCCG GACGGGGACG TGCTCACTCG CGACGGCGCC GACGAGATCC 501                                                550
  RdCVF1    ~~~~~~~~~~ ~~~~~~~~~~ ~~~~~~~~~~ ~~~~~~~~~~ ~~~~~~~~~~
bg299078    CCACACCAAC CACAGGCGAC AACAACACAC AAGAGGTGTC CCATCCGCTC
ai716631    ~~~~~~~~~~ ~~~~~~~~~~ ~~~~~~~~~~ ~~~~~~~~~~ ~~~~~~~~~~
bg294111    AGCGTCTGGG ACCCGCCTGC TTTGCCAACT GGCAGGAGGC CGCAGAGCTC
be108041    ~~~~~~~~~~ ~~~~~~~~~~ ~~~~~~~~~~ ~~~~~~~~~~ ~~~~~~~~~~
bg395178    AGCGCCTGGG CACCGCCTGC TTCGCCAACT GGCAGGAGGC GGCCGAGGTG 551                                                600
  RdCVF1    ~~~~~~~~~~ ~~~~~~~~~~ ~~~~~~~~~~ ~~~~~~~~~~ ~~~~~~~~~~
bg299078    TTCCATCACA GCCCACTGAC GCCAGACAGC ATCGCGACGC TCACGGCTCA
ai716631    ~~~~~~~~~~ ~~~~~~~~~~ ~~~~~~~~~~ ~~~~~~~~~~ ~~~~~~~~~~
bg294111    CTGGACCGCA GCTTCCTGCA ACCGGAGGAT TTGGATGAGC CTGCGCGGCG
be108041    ~~~~~~~~~~ ~~~~~~~~~~ ~~~~~~~~~~ ~~~~~~~~~~ ~~~~~~~~~~
bg395178    CTGGACCGCA ACTTCCAGCT GCCAGAGGAC CTGGAGGACC AGGAGCCACG 601                                                650
  RdCVF1    ~~~~~~~~~~ ~~~~~~~~~~ ~~~~~~~~~~ ~~~~~~~~~~ ~~~~~~~~~~
bg299078    GAAAAACACA GGTAGTCTCA CAGGCCTGCC ATCCTAATAC TGGCCACCCT
ai716631    ~~~~~~~~~~ ~~~~~~~~~~ ~~~~~~~~~~ ~~~~~~~~~~ ~~~~~~~~~~
bg294111    CAGCATCACC GAGCCTCTGC GCCGTCGCAA GTACCGAGTA GACCGGGATG
be108041    ~~~~~~~~~~ ~~~~~~~~~~ ~~~~~~~~~~ ~~~~~~~~~~ ~~~~~~~~~~
bg395178    GAGCCTCACC GAGTGCCTGC GCCGCCACAA GTACCGCGTG GAAAAGGCGG 651                                                700
  RdCVF1    ~~~~~~~~~~ ~~~~~~~~~~ ~~~~~~~~~~ ~~~~~~~~~~ ~~~~~~~~~~
bg299078    GAGCACAAGA GCGATGGCTA CAAGCCTCAA GGCTAGAATC TAAAACCACG
ai716631    ~~~~~~~~~~ ~~~~~~~~~~ ~~~~~~~~~~ ~~~~~~~~~~ ~~~~~~~~~~
bg294111    TCGGCGGGAG CGGGGCGAAA CGGCGCGACT CTGGTGAACC CCAGGGGGAC
be108041    ~~~~~~~~~~ ~~~~~~~~~~ ~~~~~~~~~~ ~~~~~~~~~~ ~~~~~~~~~~
bg395178    CGCGAGGCGG CGCGACCCGG GGAGGGGCT  GGGGACGGAG GCCGGGGCCC 701                                                750
  RdCVF1    ~~~~~~~~~~ ~~~~~~~~~~ ~~~~~~~~~~ ~~~~~~~~~~ ~~~~~~~~~~
bg299078    AGGTGGGGAC CGTAGGCCCC ACTCCCCGGG AGCGC~~~~~ ~~~~~~~~~~
ai716631    ~~~~~~~~~~ ~~~~~~~~~~ ~~~~~~~~~~ ~~~~~~~~~~ ~~~~~~~~~~
bg294111    GCGGGTACAA GGGCGGAGCT CTGGTGACTC CCAGGGTAGG AGTGGGGACC
be108041    ~~~~~~~~~~ ~~~~~~~~~~ ~~~~~~~~~~ ~~~~~~~~~~ ~~~~~~~~~~
bg395178    GGGGGGCTGT ACTGACCGCT GGGTGGAGCA GAGGGAGGGG GATTGGTGGA 751                                                800
  RdCVF1    ~~~~~~~~~~ ~~~~~~~~~~ ~~~~~~~~~~ ~~~~~~~~~~ ~~~~~~~~~~
bg299078    ~~~~~~~~~~ ~~~~~~~~~~ ~~~~~~~~~~ ~~~~~~~~~~ ~~~~~~~~~~
ai716631    ~~~~~~~~~~ ~~~~~~~~~~ ~~~~~~~~~~ ~~~~~~~~~~ ~~~~~~~~~~
bg294111    GGAGCTCTGG TGACACCAAA GTACCGGTGC ACGACCGAGG TTGATGACCC
be108041    ~~~~~~~~~~ ~~~~~~~~~~ ~~~~~~~~~~ ~~~~~~~~~~ ~~~~~~~~~~
bg395178    AGAACAACAA CCACACGCAG CCAGCACCAG GTATCCCGAC TAGGGGAGAC 801                                                850
  RdCVF1    ~~~~~~~~~~ ~~~~~~~~~~ ~~~~~~~~~~ ~~~~~~~~~~ ~~~~~~~~~~
bg299078    ~~~~~~~~~~ ~~~~~~~~~~ ~~~~~~~~~~ ~~~~~~~~~~ ~~~~~~~~~~
ai716631    ~~~~~~~~~~ ~~~~~~~~~~ ~~~~~~~~~~ ~~~~~~~~~~ ~~~~~~~~~~
bg294111    TCCCGAAGGA ACCGG~~~~~ ~~~~~~~~~~ ~~~~~~~~~~ ~~~~~~~~~~
be108041    ~~~~~~~~~~ ~~~~~~~~~~ ~~~~~~~~~~ ~~~~~~~~~~ ~~~~~~~~~~
bg395178    AGGGCGAAGA CCTGACCCAA AGCACAACCA CCGGGGACAC TAAACGACTC 851                                                900
  RdCVF1    ~~~~~~~~~~ ~~~~~~~~~~ ~~~~~~~~~~ ~~~~~~~~~~ ~~~~~~~~~~
```

Figure 13: (continued)

```
bg299078    ~~~~~~~~~~  ~~~~~~~~~~  ~~~~~~~~~~  ~~~~~~~~~~  ~~~~~~~~~~
ai716631    ~~~~~~~~~~  ~~~~~~~~~~  ~~~~~~~~~~  ~~~~~~~~~~  ~~~~~~~~~~
bg294111    ~~~~~~~~~~  ~~~~~~~~~~  ~~~~~~~~~~  ~~~~~~~~~~  ~~~~~~~~~~
be108041    ~~~~~~~~~~  ~~~~~~~~~~  ~~~~~~~~~~  ~~~~~~~~~~  ~~~~~~~~~~
bg395178    AACTCAATCC  TGTGGGCACC  AGGACACCGC  AAAAAAAAAC  AAAAAAAGCA 901                     929
   RdCVF1   ~~~~~~~~~~  ~~~~~~~~~~  ~~~~~~~~~
bg299078    ~~~~~~~~~~  ~~~~~~~~~~  ~~~~~~~~~
ai716631    ~~~~~~~~~~  ~~~~~~~~~~  ~~~~~~~~~
bg294111    ~~~~~~~~~~  ~~~~~~~~~~  ~~~~~~~~~
be108041    ~~~~~~~~~~  ~~~~~~~~~~  ~~~~~~~~~
bg395178    AAATGCAAAA  AAAGACAGGA  CATACGACG
```

Figure 14:

BG299078   SEQ ID NO: 15

```
      ATCGGATCCTCTCTGGGTCCCCAGCTCCTTGCATACTGCTACCATGGCATCTCTCTTCTC
1     ----------+----------+----------+----------+----------+----------+  60
      TAGCCTAGGAGAGACCCAGGGGTCGAGGAACGTATGACGATGGTACCGTAGAGAGAAGAG

TGGACGCATCTTGATCAGGAACAACAGCGACCAGGATGAAGTGGAGACAGAGGCAGAGCT
61    ----------+----------+----------+----------+----------+----------+ 120
      ACCTGCGTAGAACTAGTCCTTGTTGTCGCTGGTCCTACTTCACCTCTGTCTCCGTCTCGA

GAGCCGTAGGTTAGAGAATCGTCTGGTGTTGCTGTTCTTCGGCGCCGGCGCCTGTCCCCA
121   ----------+----------+----------+----------+----------+----------+ 180
      CTCGGCATCCAATCTCTTAGCAGACCACAACGACAAGAAGCCGCGGCCGCGGACAGGGGT
                  +T
      GTGCCAGGCCTTGCCCCAGTCCTCAAAGACTTCTTCGTGCGGCTCACTGACGAGTTCTAC
181   ----------+----------+----------+----------+----------+----------+ 240
      CACGGTCCGGAACGGGGTCAGGAGTTTCTGAAGAAGCACGCCGAGTGACTGCTCAAGATG

GTGCTGCGGGCAGCACAGCTGGCCCTGGTCTATGTGTCCCAGGACCCTACAGAGGAGCAA
241   ----------+----------+----------+----------+----------+----------+ 300
      CACGACGCCCGTCGTGTCGACCGGGACCAGATACACAGGGTCCTGGGATGTCTCCTCGTT
                                                           removed
      CAGGACCTCTTCCTCAGGGACATGCCTGAAAAATGGCTCTTCCTGCCGTCCCACTGATGA
301   ----------+----------+----------+----------+----------+----------+ 360
      GTCCTGGAGAAGGAGTCCCTGTACGGACTTTTTACCGAGAAGGACGGCAGGGTGACTACT ACTGAGGAGGTGAGGCCCCAGGGAAGACCAGGGAGGGCTTCCTGGAGAAGGCATTTCCCT
361   ----------+----------+----------+----------+----------+----------+ 420
      TGACTCCTCCACTCCGGGGTCCCTTCTGGTCCCTCCCGAAGGACCTCTTCCGTAAAGGGA GGAGGTTTACTGTCCTGGTACTACTTGTGCACTAAAGAGGTATTCCTCCACACCAACCAC
421   ----------+----------+----------+----------+----------+----------+ 480
      CCTCCAAATGACAGGACCATGATGAACACGTGATTTCTCCATAAGGAGGTGTGGTTGGTG AGGCGACAACAACACACAAGAGGTGTCCCATCCGCTCTTCCATCACAGCCCACTGACGCC
481   ----------+----------+----------+----------+----------+----------+ 540
      TCCGCTGTTGTTGTGTGTTCTCCACAGGGTAGGCGAGAAGGTAGTGTCGGGTGACTGCGG AGACAGCATCGCGACGCTCACGGCTCAGAAAAACACAGGTAGTCTCACAGGCCTGCCATC
541   ----------+----------+----------+----------+----------+----------+ 600
      TCTGTCGTAGCGCTGCGAGTGCCGAGTCTTTTTGTGTCCATCAGAGTGTCCGGACGGTAG
```

Figure 14: (continued)

```
    CTAATACTGGCCACCCTGAGCACAAGAGCGATGGCTACAAGCCTCAAGGCTAGAATCTAA
601 ---------+---------+---------+---------+---------+---------+ 660
    GATTATGACCGGTGGGACTCGTGTTCTCGCTACCGATGTTCGGAGTTCCGATCTTAGATT

AACCACGAGGTGGGGACCGTAGGCCCCACTCCCCGGGAGCGC
661 ---------+---------+---------+---------+-- 702
    TTGGTGCTCCACCCCTGGCATCCGGGGTGAGGGGCCCTCGCG
```

Figure 15:

BG294111 SEQ ID NO: 17

```
    CAGCTCCTTGCATACTGCTACCATGGCATCTCTCTTCTCTGGACGCATCTTGATCAGGAA
1   ---------+---------+---------+---------+---------+---------+ 60
    GTCGAGGAACGTATGACGATGGTACCGTAGAGAGAAGAGACCTGCGTAGAACTAGTCCTT

CAACAGCGACCAGGATGAAGTGGAGACAGAGGCAGAGCTGAGCCGTAGGTTAGAGAATCG
61  ---------+---------+---------+---------+---------+---------+ 120
    GTTGTCGCTGGTCCTACTTCACCTCTGTCTCCGTCTCGACTCGGCATCCAATCTCTTAGC
      +T                                             +T
    TCTGGTGTGCTGTTCTTCGGCGCCGGCGCCTGTCCCCAGTGCCAGGCCTTGCCCCAGTCC
121 ---------+---------+---------+---------+---------+---------+ 180
    AGACCACACGACAAGAAGCCGCGGCCGCGGACAGGGGTCACGGTCCGGAACGGGGTCAGG

TCAAAGACTTCTTCGTGCGGCTCACTGACGAGTTCTACGTGCTGCGGGCAGCACAGCTGG
181 ---------+---------+---------+---------+---------+---------+ 240
    AGTTTCTGAAGAAGCACGCCGAGTGACTGCTCAAGATGCACGACGCCCGTCGTGTCGACC

CCCTGGTCTATGTGTCCCAGGACCCTACAGAGGAGCAACAGGACCTCTTCCTCAGGGACA
241 ---------+---------+---------+---------+---------+---------+ 300
    GGGACCAGATACACAGGGTCCTGGGATGTCTCCTCGTTGTCCTGGAGAAGGAGTCCCTGT

TGCCTGAAAAATGGCTCTTCCTGCCGTTCCATGATGAACTGAGGAGGGACCTCGGGCGCC
301 ---------+---------+---------+---------+---------+---------+ 360
    ACGGACTTTTTACCGAGAAGGACGGCAAGGTACTACTTGACTCCTCCCTGGAGCCCGCGG

AGTTCTCTGTCCGTCAACTGCCAGCGGTTGTGGTACTTAAGCCTGGTGGGGACGTGCTGA
361 ---------+---------+---------+---------+---------+---------+ 420
    TCAAGAGACAGGCAGTTGACGGTCGCCAACACCATGAATTCGGACCACCCCTGCACGACT

CAAGCGACGCCACGGAGGAGATCCAGCGTCTGGGACCCGCCTGCTTTGCCAACTGGCAGG
421 ---------+---------+---------+---------+---------+---------+ 480
    GTTCGCTGCGGTGCCTCCTCTAGGTCGCAGACCCTGGGCGGACGAAACGGTTGACCGTCC

AGGCCGCAGAGCTCCTGGACCGCAGCTTCCTGCAACCGGAGGATTTGGATGAGCCTGCGC
481 ---------+---------+---------+---------+---------+---------+ 540
    TCCGGCGTCTCGAGGACCTGGCGTCGAAGGACGTTGGCCTCCTAAACCTACTCGGACGCG

GGCGCAGCATCACCGAGCCTCTGCGCCGTCGCAAGTACCGAGTAGACCCGGATGTCGGCG
541 ---------+---------+---------+---------+---------+---------+ 600
    CCGCGTCGTAGTGGCTCGGAGACGCGGCAGCGTTCATGGCTCATCTGGCCCTACAGCCGC

GGAGCGGGGCGAAACGGCGCGACTCTGGTGAACCCCAGGGGGACGCGGGTACAAGGGCGG
601 ---------+---------+---------+---------+---------+---------+ 660
    CCTCGCCCCGCTTTGCCGCGCTGAGACCACTTGGGGTCCCCCTGCGCCCATGTTCCCGCC

AGCTCTGGTGACTCCCAGGGTAGGAGTGGGGACCGGAGCTCTGGTGACACCAAAGTACCG
661 ---------+---------+---------+---------+---------+---------+ 720
```

Figure 15: (continued)

```
        TCGAGACCACTGAGGGTCCCATCCTCACCCCTGGCCTCGAGACCACTGTGGTTTCATGGC

GTGCACGACCGAGGTTGATGACCCTCCCGAAGGAACCGG
    721 ---------+---------+---------+--------- 759
        CACGTGCTGGCTCCAACTACTGGGAGGGCTTCCTTGGCC
```

Figure 16:
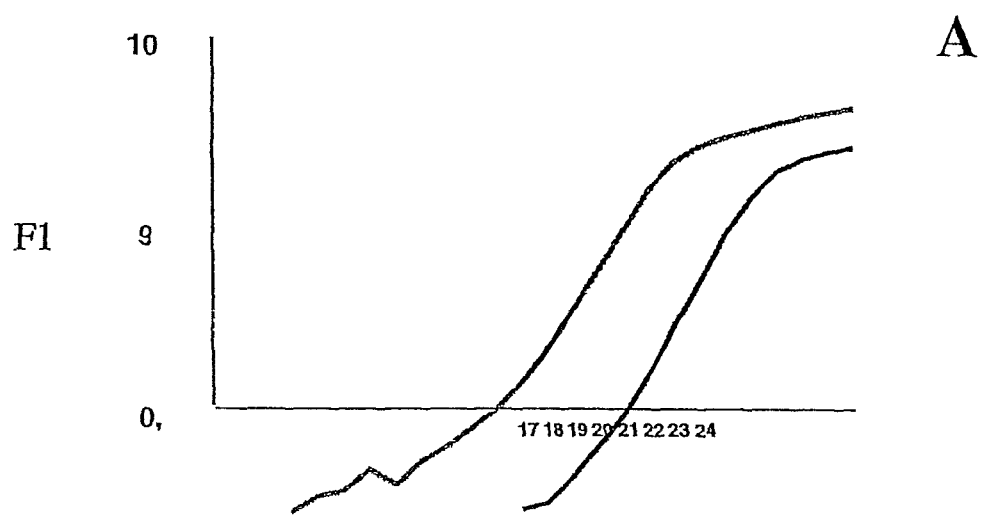
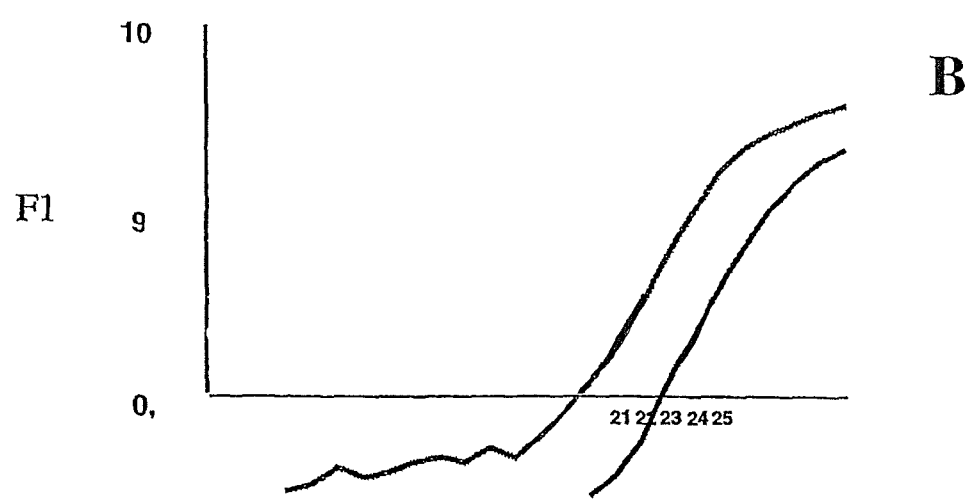

METHODS OF TREATING RETINITIS PIGMENTOSA USING NUCLEIC ACIDS ENCODING RDCVF1 OR RDCVF2

RELATED APPLICATIONS

The present application is a divisional of U.S. patent application Ser. No. 13/348,435, filed Jan. 11, 2012, now U.S. Pat. No. 8,518,695, which is a continuation of U.S. patent application Ser. No. 11/739,739, filed Apr. 25, 2007, now U.S. Pat. No. 8,114,849, which is a divisional of U.S. patent application Ser. No. 10/473,008, filed Apr. 2, 2004, now U.S. Pat. No. 7,795,387, which claims the benefit of and which is a national stage filing of International Application No. PCT/EP2002/003810, filed on Apr. 5, 2002, which claims priority to, and the benefit of, French Patent Application No. 0104712, filed Apr. 6, 2001, the contents of which are hereby incorporated by reference in their entirety.

FIELD OF THE INVENTION

This invention relates to methods and compositions for detection and treatment of retinal degenerative diseases. In particular, the invention relates to a protein that protects against cone degeneration, nucleic acid molecules that encode such a protein, antibodies that recognize the protein, and methods for diagnosing retinal degenerative diseases.

BACKGROUND OF THE INVENTION

Photoreceptors are a specialized subset of retinal neurons, that are responsible for vision. Photoreceptors consist of rods and cones which are the photosensitive cells of the retina. Each rod and cone elaborates a specialized cilium, referred to as an outer segment, that houses the phototransduction machinery. The rods contain a specific light-absorbing visual pigment, rhodopsin. There are three classes of cones in humans, characterized by the expression of distinct visual pigments: the blue cone, green cone and red cone pigments. Each type of visual pigment protein is tuned to absorb light maximally at different wavelengths. The rod rhodopsin mediates scotopic vision (in dim light), whereas the cone pigments are responsible for photopic vision (in bright light). The red, blue and green pigments also form the basis of color vision in humans. The visual pigments in rods and cones respond to light and generate an action potential in the output cells, the rod bipolar neurons, which is then relayed by the retinal ganglion neurons to produce a visual stimulus in the visual cortex.

In humans, a number of diseases of the retina involve the progressive degeneration and eventual death of photoreceptors, leading inexorably to blindness. Degeneration of photoreceptors, such as by inherited retinal dystrophies (e.g., retinitis pigmentosa), agerelated macular degeneration and other maculopathies, or retinal detachment, are all characterized by the progressive atrophy and loss of function of photoreceptor outer segments. In addition, death of photoreceptors or loss of photoreceptor function results in partial deafferentation of second order retinal neurons (rod bipolar cells and horizontal cells) in patients with retinal dystrophies, thereby decreasing the overall efficiency of the propagation of the electrical signal generated by photoreceptors. Secondary glial and pigment epithelium changes secondary to photoreceptors degeneration result in vascular changes leading to ischemia and gliosis. Trophic factors that are capable of rescuing photoreceptors from cell death and/or restoring the function of dysfunctional (atrophic or dystrophic) photoreceptors may represent useful therapies for the treatment of such conditions.

The progression of these conditions points to a sequential loss of the two classes of photoreceptors: initially rods are lost as a direct result of a genetic or environmental or unknown lesion, resulting in night blindness and a reduction in visual field followed inevitably by loss of cones leading to total blindness. Thus, cones die indirectly since they do not express the primary lesion.

Not all of the genes associated with retinal dystrophy have yet been identified. Identification of such genes would make possible to both diagnose the disease and identify effective therapies.

SUMMARY OF THE INVENTION

The invention relates generally to a novel gene family, Rod-derived Cone Viability Factor (Rdcvf). In a first aspect, the invention provides an isolated polypeptide with an amino acid sequence as set forth in SEQ ID NO:2 or SEQ ID NO:4. Such a polypeptide, or fragments thereof, is found in the eye of sufferers of retinal dystrophies to a much lesser extent than in the eye of individuals without retinal dystrophy. Fragments of the isolated polypeptide with an amino acid sequence as set forth in SEQ ID NO:2 or SEQ ID NO:4 will comprise polypeptides comprising from about 5 to 10 amino acids, preferably from about 10 to about 20 amino acids, more preferably from about 20 to about 100 amino acids, and most preferably from about 20 to about 50 amino acids. In accordance with this aspect of the invention there are provided a novel polypeptide of mammalian origin, and in particular of mouse or human origin as well as biologically, diagnostically or therapeutically useful fragments, variants and derivatives thereof, variants and derivatives of the fragments, and analogs of the foregoing. Also within the scope of the present invention are polypeptides that are substantially similar to the polypeptide with the amino acid sequence as set forth in SEQ ID NO:2 or SEQ ID NO:4 e.g. an amino acid sequence as set forth in SEQ ID NO: 6, SEQ ID NO: 8, SEQ ID NO: 10, SEQ ID NO: 12 and SEQ ID NO: 14.

In a second aspect, the invention provides an isolated nucleic acid molecule comprising a nucleotide sequence as set forth in SEQ ID NO:1 or SEQ ID NO:3. Also within the scope of the present invention are nucleic acids that are substantially similar to the nucleic acid with the nucleotide sequence as set forth in SEQ ID NO:1 or SEQ ID NO:3 e.g. nucleotide sequences as set forth in SEQ ID NO: 5, SEQ ID NO: 7, SEQ ID NO: 9, SEQ ID NO: 11 or SEQ ID NO: 13. In a preferred embodiment, the invention provides an isolated nucleic acid molecule that encodes for a polypeptide selected from the group consisting of the polypeptides set forth in SEQ ID NO:2, SEQ ID NO:4, SEQ ID NO:6, SEQ ID NO:8, SEQ ID NO:10, SEQ ID NO:12 and SEQ ID NO:14, e.g. nucleotides 45-374 of SEQ ID NO:1, nucleotides 26-676 of SEQ ID NO:3, nucleotides 24-353 of SEQ ID NO:5, nucleotides 48-686 of SEQ ID NO:7, nucleotides 265-570 of SEQ ID NO:9, nucleotides 300-770 of SEQ ID NO: 11 or nucleotides 331-738 of SEQ ID NO:13. In a preferred embodiment, the isolated DNA takes the form of a vector molecule comprising the DNA as set forth in SEQ ID NO:1 or SEQ ID NO:3.

A third aspect of the present invention encompasses a method for the diagnosis of retinal dystrophy in a human which includes detecting the decreased transcription of messenger RNA transcribed from Rdcvf1 or Rdcvf2-encoding DNA in the eye from a mammalian organism, preferably a human, where such decreased transcription is diagnostic of the organisms' affliction with retinal dystrophy or pathological aging (ARMD). Another embodiment of the assay aspect of the invention provides a method for the diagnosis of retinal dystrophy in a mammalian organism, preferably a human, which requires measuring the amount of a Rdcvf1 or Rdcvf2 polypeptide or fragments thereof in the eye of a human suspected of suffering form a retinal dystrophy, where the presence of a decreased amount of the polypeptide or fragments thereof, relative to the amount of the polypeptide or fragments thereof in the eye of an individual not suffering from a retinal dystrophy, is diagnostic of the human's suffering from retinal dystrophy.

In accordance with another aspect of the invention there are provided anti-sense polynucleotides that regulate transcription of the Rdcvf1 or Rdcvf2 gene; in another embodiment, double stranded RNA is provided that can regulate the transcription of the Rdcvf1 or Rdcvf2 gene.

Another aspect of the invention provides a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned Rdcvf1 polypeptides comprising culturing host cells having incorporated therein an expression vector containing an exogenously-derived Rdcvf1 or Rdcvf2-encoding polynucleotide under conditions sufficient for expression of Rdcvf1 or Rdcvf2 polypeptides in the host and then recovering the expressed polypeptide.

In accordance with another aspect of the invention there are provided products, compositions, processes and methods that utilize the aforementioned polypeptides and polynucleotides for, inter alia, research, biological, clinical and therapeutic purposes.

In certain additional preferred aspects of the invention there are provided an antibody or a fragment thereof which specifically binds to a polypeptide that comprises the amino acid sequence set forth in SEQ ID NO:2, SEQ ID NO:4, SEQ ID NO:6 or SEQ ID NO:8, i.e., Rdcvf1, or SEQ ID NO: 10, SEQ ID NO: 12 or SEQ ID NO: 14, i.e. Rdcvf2. In certain particularly preferred aspects in this regard, the antibodies are highly selective for mammalian, preferably mouse and in particular human Rdcvf1 or Rdcvf2 polypeptides or portions of such Rdcvf1 or Rdcvf2 polypeptides. In a related aspect, an antibody or fragment thereof is provided that binds to a fragment or portion of the amino acid sequence set forth in SEQ ID NO:2, SEQ ID NO:4, SEQ ID NO:6, SEQ ID NO:8, SEQ ID NO:10, SEQ ID NO:12 or SEQ ID NO:14.

In another aspect, methods of treating a disease in a subject, where the disease is mediated by or associated with a change in Rdcvf1 or Rdcvf2 gene expression e.g. a decrease in the presence of RDCVF1 or RDCVF2 polypeptide in the eye, by the administration of a therapeutically effective amount of a RDCVF1 or RDCVF2 protein as set out in SEQ ID NO:2 SEQ ID NO:4, SEQ ID NO:6, SEQ ID NO:8, SEQ ID NO:10, SEQ ID NO:12 or SEQ ID NO:14 or a related protein or a fragment or portion thereof to the subject is provided. Also provided are methods for the diagnosis of a disease or condition associated with an decrease in Rdcvf1 or Rdcvf2 gene expression or decrease in the presence of RDCVF1 or RDCVF2 polypeptide in a subject, which comprises utilizing an antibody that binds to a polypeptide with the amino acid sequence set out in SEQ ID NO:2, SEQ ID NO:4, SEQ ID NO:6, SEQ ID NO:8, SEQ ID NO:10, SEQ ID NO:12 or SEQ ID NO:14, or a fragment or portion thereof in an immunoassay.

In yet another aspect, the invention provides cells which can be propagated in vitro, preferably vertebrate cells, which are capable upon growth in culture of producing a polypeptide that comprises the amino acid sequence set forth in SEQ ID NO:2, SEQ ID NO:4, SEQ ID NO:6, SEQ ID NO:8, SEQ ID NO:10, SEQ ID NO:12 or SEQ ID NO:14 or fragments thereof, where the cells contain transcriptional control DNA sequences, other than mouse or human Rdcvf1 or Rdcvf2 transcriptional control sequences, where the transcriptional control sequences control transcription of DNA encoding a polypeptide with the amino acid sequence according to SEQ ID NO:2, SEQ ID NO:4, SEQ ID NO:6, SEQ ID NO:8, SEQ ID NO:10, SEQ ID NO:12 or SEQ ID NO:14 or fragments thereof.

In a related aspect, the present invention provides a method for producing Rdcvf1 or Rdcvf2 polypeptides which comprises culturing a host cell having incorporated therein an expression vector containing an exogenously-derived Rdcvf1 or Rdcvf2-encoding polynucleotide under conditions sufficient for expression of Rdcvf1 or Rdcvf2 polypeptides in the host cell, thereby causing the production of an expressed polypeptide, and recovering the expressed polypeptide.

In yet another aspect of the present invention there are provided assay methods and kits comprising the components necessary to detect abnotinal, e.g. below-normal expression of Rdcvf1 or Rdcvf2 polynucleotides or polypeptides or fragments thereof in body tissue samples derived from a patient, such kits comprising e.g., antibodies that bind to Rdcvf1 or Rdcvf2 or oligonucleotide probes that hybridize with polynucleotides of the invention. In a preferred embodiment, such kits also comprise instructions detailing the procedures by which the kit components are to be used.

In another aspect, the invention is directed to an Rdcvf1 or Rdcvf2 polypeptide for use in the treatment of a human or animal body. A related aspect is directed to the use of an Rdcvf1 or Rdcvf2 polypeptide or fragment thereof, nucleotide encoding Rdcvf1 or Rdcvf2 or a fragment thereof, or antibody that binds to Rdcvf1 or Rdcvf2 or a fragment thereof in the manufacture of a medicament to treat a retinal dystrophy.

In another aspect, the invention provides a retinoprotective agent comprising a polypeptide selected from the group of SEQ ID NO:2, SEQ ID NO:4, SEQ ID NO:6, SEQ ID NO:8, SEQ ID NO:10, SEQ ID NO:12 or SEQ ID NO:14, and, optionally, a pharmaceutically acceptable carrier. In a related aspect the invention provides a pharmaceutical compositions comprising a Rdcvf1 or Rdcvf2 polypeptide or fragment thereof, nucleotide encoding Rdcvf1 or Rdcvf2 or a fragment thereof, for the treatment of a retinal dystrophy. In another related aspect, the invention provides a pharmaceutical composition comprising a therapeutically effective amount of a polypeptide selected from the group of SEQ ID NO:2, SEQ ID NO:4, SEQ ID NO:6, SEQ ID NO:8, SEQ ID NO:10, SEQ ID NO:12 or SEQ ID NO:14 and a pharmaceutically acceptable carrier.

In a related aspect, the invention provides a method for the treatment of retinal dystrophy comprising administering a therapeutically effective amount of a polypeptide selected from the group of SEQ ID NO:2, SEQ ID NO:4, SEQ ID NO:6, SEQ ID NO:8, SEQ ID NO:10, SEQ ID NO:12 or SEQ ID NO:14, and pharmaceutically acceptable carrier, to a subject in need.

In another aspect, the invention is directed to methods for the identification of molecules that can bind to Rdcvf1 or Rdcvf2 and/or modulate the activity of Rdcvf1 or Rdcvf2 or molecules that can bind to nucleic acid sequences that modulate the transcription or translation of Rdcvf1 or Rdcvf2. Such methods are disclosed in, e.g., U.S. Pat. Nos. 5,541,070; 5,567,317; 5,593,853; 5,670,326; 5,679,582; 5,856,083;

5,858,657; 5,866,341; 5,876,946; 5,989,814; 6,010,861; 6,020,141; 6,030,779; and 6,043,024, all of which are incorporated by reference herein in their entirety. Molecules identified by such methods also fall within the scope of the present invention.

In yet another aspect, the invention is directed to methods for the introduction of nucleic acids of the invention into one or more tissues of a subject in need of treatment with the result that one or more proteins encoded by the nucleic acids are expressed and or secreted by cells within the tissue.

In another aspect the invention provides a method of providing photoreceptor cells for implantation wherein the photoreceptor cells are cultured together with RdCVF1 or RdCVF2.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 1: mouse Rdcvf1 nucleotide sequence from the expression cloning and mouse RdCVF1 amino acid sequence.

FIG. 2: mouse Rdcyf1L nucleotide sequence, and amino acid sequence.

FIG. 3: human Rdcvf1 and human Rdcvf1 amino acids sequence.

FIG. 4: human Rdcyf1L nucleotide sequence. human Rdcyf1L amino acids sequence.

FIG. 5: mouse Rdcvf2 nucleotide sequence and: mouse Rdcvf2 amino acids.

FIG. 6: mouse Rdcvf2L nucleotide sequence and mouse Rdcvf2L amino acid.

FIG. 7: human Rdcvf2 nucleotide sequence. and human Rdcvf2 amino acids sequence.

FIG. 8: depicts an amino acid alignments of the short forms of Rdcvf: (SEQ ID No 2, 6, 10 and 14) and of the long forms of Rdcvf: SEQ ID No4, 8, 12 and 14).

FIG. 9: depicts the primers for GST-Rdcvf1.

FIG. 10: Multiple Alignment of RDCVF1 (SEQ ID NO: 2)/RDCVF2 (SEQ ID NO: 10).

FIG. 11: Comparison of mouse (SEQ ID NO: 10) and human (SEQ ID NO: 36) RDCVF2

FIG. 12: Multiple Alignment of mouse Rdcvf2 (SEQ ID NO: 37) with EST clones be552141 (SEQ ID NO: 20), bi517442 (SEQ ID NO: 21), bg707818 (SEQ ID NO: 22) and bi603812 (SEQ ID NO: 23).

FIG. 13: Multiple Alignment of Rdcvf1 (SEQ ID NO: 38) with EST clones bg299078 (SEQ ID NO: 15), ai716631 (SEQ ID NO: 16), bg294111 (SEQ ID NO: 17), be108041 (SEQ ID NO: 18) and bg395178 (SEC, ID NO: 19).

FIG. 14: EST sequence bg299078 (SEQ ID NO: 15) corrected to match Rdcvf1.

FIG. 15: EST sequence bg294111 (SEQ ID NO: 17) corrected to match Rdcvf1L.

FIG. 16: Real-time RT-PCR analysis of the expression of rod arrestin (A) and RdCSF1 (B) in 5 weeks retina C57BL/6@N 5 weeks (gray) and C3H/HE@N (black).

DETAILED DESCRIPTION OF THE INVENTION

Figure 17:
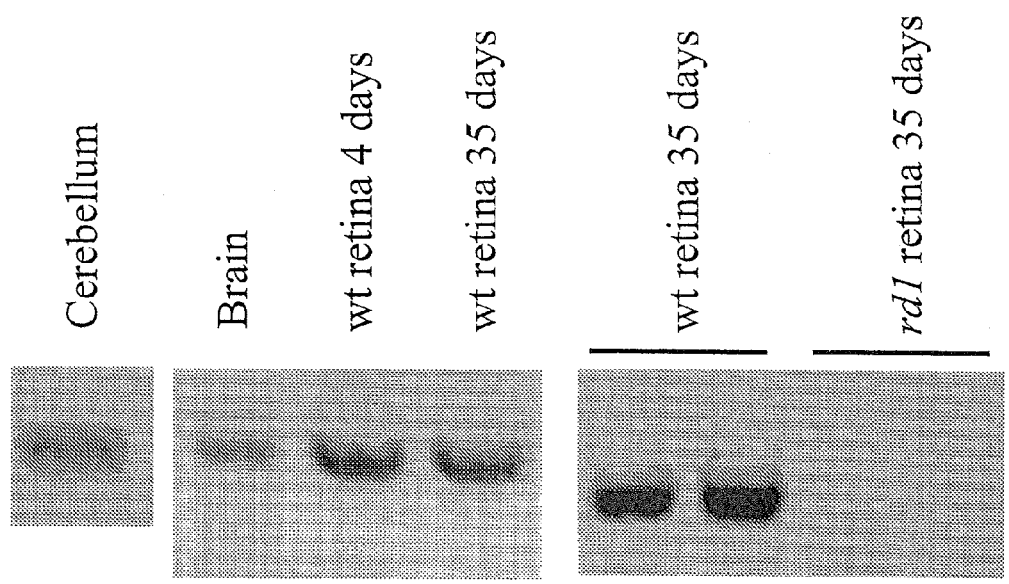
FIG. 17: RT-PCR analysis showing that Rdcvf2 is expressed in a rod-dependent manner and is expressed in another part of the CNS.
Figure 18:
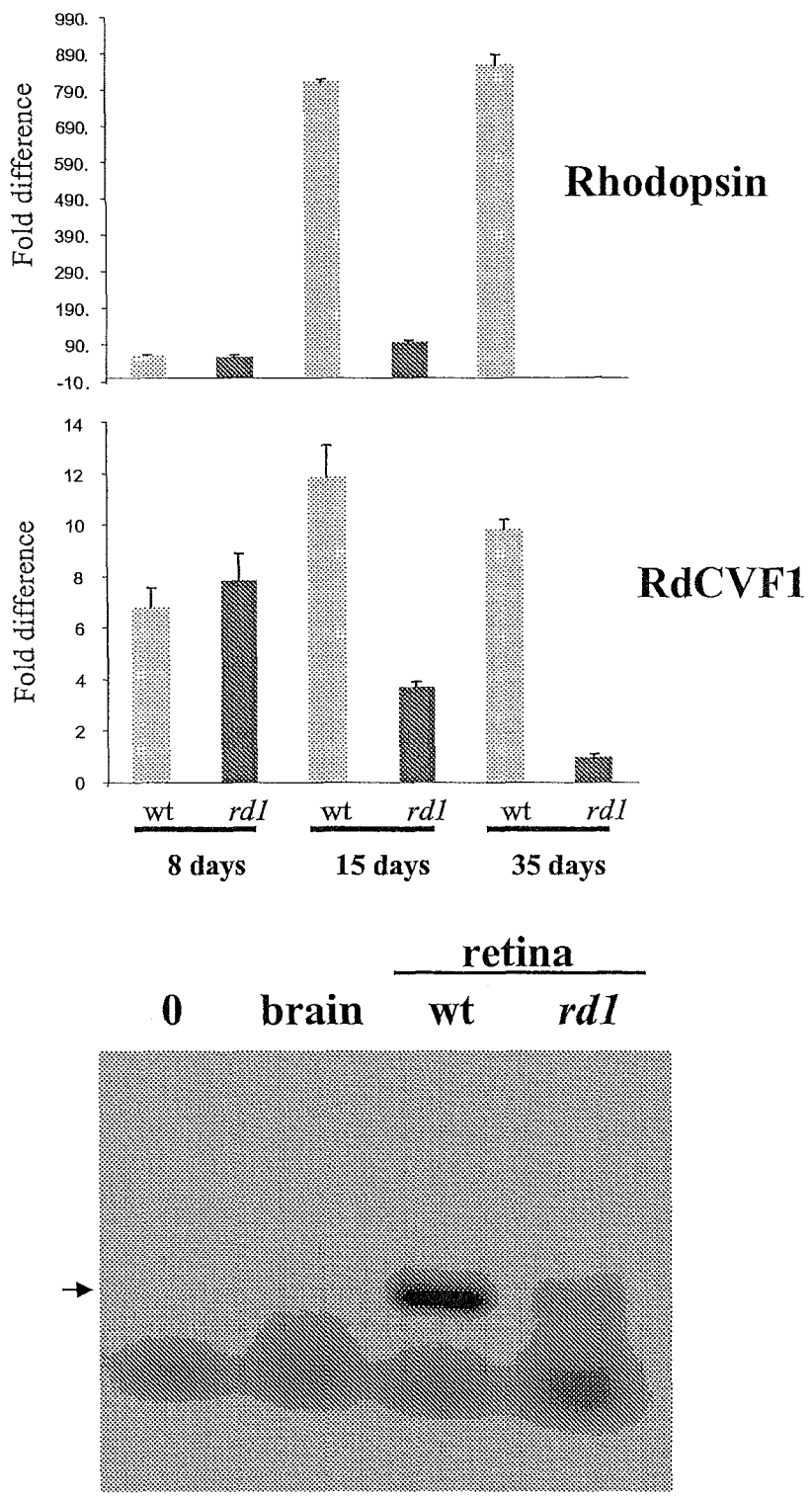
FIG. 18: PCR analysis showing that RdCVF1 is expressed in a rod-dependent manner.

All patent applications, patents and literature references cited herein are hereby incorporated by reference in their entirety.

In practicing the present invention, many conventional techniques in molecular biology, microbiology, and recombinant DNA are used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

As used herein, "differentially expressed gene" refers to (a) a gene containing at least one of the DNA sequences disclosed herein (e.g., as shown in FIG. 1 and SEQ ID NO:1 or as shown in FIG. 2 and SEQ ID NO:3); (b) any DNA sequence that encodes the amino acid sequence encoded by the DNA sequences disclosed herein (e.g., as shown in FIG. 1 and SEQ ID NO:2 or as shown in FIG. 2 and SEQ ID NO:4); or (c) any DNA sequence that is substantially similar to the coding sequences disclosed herein.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. Where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 90%, more preferably at least 95%, still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0. The localS program, version 1.16, is used with the following parameters: match: 1, mismatch penalty: 0.33, open-gap penalty: 2, extended-gap penalty: 2. A nucleotide sequence "substantially similar" to the reference nucleotide sequence hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C., yet still encodes a functionally equivalent gene product.

The differentially expressed genes disclosed herein are expressed in eye tissue and in particular is produced in rod cells however, in a human afflicted with a retinal dystrophy such as retinitus pigmentosa, age-related macular degeneration, Bardet-Biedel syndrome, Bassen-kornzweig syndrome, best disease, choroidema, gyrate atrophy, congenital amourosis, refsun syndrome, stargardt disease and Usher syndrome it is produced in decreases amounts relative to, i.e., to a lesser extent than in the corresponding tissues of humans who do not suffer from retinal dystrophy. Messenger RNA transcribed from the differentially expressed genes, and protein translated from such mRNA, is present in rod tissues and/or associated with such tissues in an amount at least about half, preferably at least about five times, more preferably at least amount ten times, most preferably at least about 100 times less than the levels of rnRNA and protein found in corresponding tissues found in humans who do not suffer from a retinal dystrophy. Such decreases transcription of Rdcvf1 or Rdcvf2 mRNA is referred to herein as "decreased transcription."

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and the like.

"Heterologous" as used herein means "of different natural origin" or represent a non-natural state. For example, if a host cell is transformed with a DNA or gene derived from another organism, particularly from another species, that gene is heterologous with respect to that host cell and also with respect to descendants of the host cell which carry that gene. Similarly, heterologous refers to a nucleotide sequence derived from and inserted into the same natural, original cell type, but which is present in a non-natural state, e.g. a different copy number, or under the control of different regulatory elements.

A vector molecule is a nucleic acid molecule into which heterologous nucleic acid may be inserted which can then be introduced into an appropriate host cell. Vectors preferably have one or more origin of replication, and one or more site into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes."

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

As used herein, the term "transcriptional control sequence" refers to DNA sequences, such as initiator sequences, enhancer sequences, and promoter sequences, which induce, repress, or otherwise control the transcription of protein encoding nucleic acid sequences to which they are operably linked.

As used herein, "Rdcvf1 transcriptional control sequences" or "Rdcvf2 transcriptional control sequences" are any of those transcriptional control sequences normally found associated with a mammalian Rdcvf1 or Rdcvf2 gene, preferably with the Rdcvf2 gene as found in the mouse or human genome.

As used herein, "non-human transcriptional control sequence" is any transcriptional control sequence not found in the human genome.

The term "polypeptide" is used interchangeably herein with the terms "polypeptides" and "protein(s)".

As used herein, a "chemical derivative" of a polypeptide of the invention is a polypeptide of the invention that contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in Remington's Pharmaceutical Sciences, 16th ed., Mack Publishing Co., Easton, Pa. (1980).

As used herein, a "neuroprotective agent" is a compound that prevents or protects neuronal cells from degeneration. A "retinoprotective agent" is a compound that prevents or protects retinal cells from degeneration.

The invention includes nucleic acid molecules, preferably DNA molecules, such as (1) an isolated comprising a nucleotide sequence as set forth in SEQ ID NO:1 or SEQ ID NO:3, (2) isolated nucleic acid molecules that comprise nucleic acid sequences that hybridize under high stringency conditions to the isolated DNA as set forth in SEQ ID NO:1 or SEQ ID NO:3, and (3) nucleic acid sequences that hybridize to (1) or (2), above. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). Suitable ranges of such stringency conditions for nucleic acids of varying compositions are described in Krause and Aaronson (1991) Methods in Enzymology, 200:546-556 in addition to Maniatis et al., cited above.

These nucleic acid molecules may act as target gene antisense molecules, useful, for example, in target gene regulation and/or as antisense primers in amplification reactions of target gene nucleic acid sequences. Further, such sequences may be used as part of ribozyme and/or triple helix sequences, also useful for target gene regulation. Still further, such molecules may be used as components of diagnostic methods whereby the presence of a RdCVF1 or RdCVF2 disease-causing allele, may be detected.

The invention also encompasses (a) vectors that contain any of the foregoing coding sequences (i.e., sense) and/or their complements (i.e., antisense); (b) expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression.

The invention includes fragments of any of the nucleic acid sequences disclosed herein. Fragments of the full length Rdcvf1 or Rdcvf2 gene may be used as a hybridization probe for a cDNA library to isolate the full length gene and to isolate other genes which have a high sequence similarity to the Rdcvf1 or Rdcvf2 gene and similar biological activity. Probes of this type preferably have at least about 30 bases and may contain, for example, from about 30 to about 50 bases, about 50 to about 100 bases, about 100 to about 200 bases, or more than 200 bases (e.g. 300). The probe may also be used to identify a cDNA clone corresponding to a full length transcript and a genomic clone or clones that contain the complete Rdcvf1 or Rdcvf2 gene including regulatory and promoter regions, exons, and introns. An example of a screen comprises isolating the coding region of the Rdcvf1 or Rdcvf2 gene by using the known DNA sequence to synthesize an oligonucleotide probe or random priming of the isolated sequence disclosed in FIG. 1 to 8. Labeled oligonucleotides having a sequence complementary to that of the gene of the present invention are used to screen a library of human cDNA, genomic DNA to determine which individual clones of the library the probe hybridizes to.

In addition to the gene sequences described above, orthologs of such sequences, as may, for example be present in other species, may be identified and may be readily isolated, without undue experimentation, by molecular biological techniques well known in the art. Further, there may exist genes at other genetic loci within the genome that encode proteins which have extensive homology (homologs) to one or more domains of such gene products. These genes may also be identified via similar techniques. Examples of orthologs or homologues are provided in FIG. 8, 10, 11, 12 or 13.

For example, the isolated expressed gene sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately low stringent conditions. Such low stringency conditions will be well known to those of skill in the art, and will vary predictably depending on the phylogeny of specific organisms from which the library and the labeled sequences are derived. For guidance regarding such conditions see, for example, Sambrook et al. cited above.

Further, a previously unknown expressed gene-type sequence may be isolated by performing PCR using two degenerated oligonucleotide primer pools designed on the basis of amino acid sequences within the gene of interest. The template for the reaction may be cDNA obtained by reverse transcription of mRNA prepared from human or nonhuman cell lines or tissue known or suspected to express a homologue or splicing variants.

The PCR product may be subcloned and sequenced to ensure that the amplified sequences represent the sequences of a expressed gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the differentially expressed gene identified is the normal, or wild type, gene, this gene may be used to isolate mutant alleles of the gene. Such an isolation is preferable in processes and disorders which are known or suspected to have a genetic basis. Mutant alleles may be isolated from individuals either known or suspected to have a genotype which contributes to disease symptoms. Mutant alleles and mutant allele products may then be utilized in the diagnostic assay systems described below.

A cDNA of the mutant gene may be isolated, for example, by using RT-PCR, a technique which is well known to those of skill in the art. In this case, the first cDNA strand may be synthesized by hybridizing an oligo-dT oligonucleotide (or random hexamers) to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene (or by any other means). Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, from a tissue known to or suspected of expressing the gene of interest in an individual suspected of to carry the mutant allele. The normal gene or any suitable fragment thereof may then be labeled and used as a probe to identify the corresponding mutant allele in the library. The clone containing this gene may then be purified through methods routinely practiced in the art, and subjected to sequence analysis as described above.

Additionally, an expression library can be constructed utilizing DNA isolated from or cDNA synthesized from a tissue known to or suspected of expressing the gene of interest in an individual suspected of to carry the mutant allele. In this manner, gene products made by the putatively mutant tissue may be expressed and screened using standard antibody screening techniques in conjunction with antibodies raised against the normal gene product, as described, below. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described above.

Differentially expressed gene products include those proteins encoded by nucleotide sequence set forth in SEQ ID NO:1, SEQ ID NO:3, SEQ ID NO:5, SEQ ID NO:7, SEQ ID NO:9, SEQ ID NO:11 or SEQ ID NO:13, in particular, a polypeptide that is or includes the amino acid sequence set out in SEQ ID NO:2, SEQ ID NO:4, SEQ ID NO:6, SEQ ID NO:8, SEQ ID NO:10, SEQ ID NO:12 or SEQ ID NO:14, or fragments thereof.

In addition, expressed gene products may include proteins that represent functionally equivalent gene products. Such an equivalent gene product may contain deletions, additions or substitutions of amino acid residues within the amino acid sequence encoded by the differentially expressed gene sequences described, above, but which result in a silent change, thus producing a functionally equivalent differentially expressed gene product (polymorphisms). Amino acid substitutions may be made on the basis of similarity in polarity, charge, solubility, hydrophobicity, hydrophilicity, and/or the amphipathic nature of the residues involved and on comparison with amino-acids sequence from other species.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent," as utilized herein, may refer to a protein or polypeptide capable of exhibiting a substantially similar in vivo or in vitro activity as the endogenous differentially expressed gene products encoded by the differentially expressed gene sequences described above. "Functionally equivalent" may also refer to proteins or polypeptides capable of interacting with other cellular or extracellular molecules in a manner similar to the way in which the corresponding portion of the endogenous differentially expressed gene product would. For example, a "functionally equivalent" peptide would be able, in an immunoassay, to diminish the binding of an antibody to the corresponding peptide (i.e., the peptidic amino acid sequence of which was modified to achieve the "functionally equivalent" peptide) of the endogenous protein, or to the endogenous protein itself, where the antibody was raised against the corresponding peptide of the endogenous protein. An equimolar concentration of the functionally equivalent peptide will diminish the aforesaid binding of the corresponding peptide by at least about 5%, preferably between about 5% and 10%, more preferably between about 10% and 25%, even more preferably between about 25% and 50%, and most preferably between about 40% and 50%.

The differentially expressed gene products may be produced by recombinant DNA technology using techniques well known in the art. Thus, methods for preparing the differentially expressed gene polypeptides and peptides of the invention by expressing nucleic acid encoding differentially expressed gene sequences are described herein. Methods which are well known to those skilled in the art can be used to construct expression vectors containing expressed gene protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA or cDNA capable of encoding expressed gene protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the differentially expressed gene coding sequences of the invention. Such host-expression systems represent vehicles by which the coding sequences of interest may be produced and subsequently purified, but also represent cells which may, when transformed or transfected with the appropriate nucleotide coding sequences, express the differentially expressed gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing differentially expressed gene protein coding sequences; yeast (e.g. *Saccharomyces, Pichia*) transformed with recombinant yeast expression vectors containing the differentially expressed gene protein coding sequences; insect cell systems infected with recombinant virus expression vectors (e.g., baculovirus) containing the differentially expressed gene protein coding sequences; plant cell systems infected with recombinant virus expression vectors (e.g., cauliflower mosaic virus, CaMV; tobacco mosaic virus, TMV) or transformed with recombinant plasmid transformation vectors (e.g., Ti plasmid) containing differentially expressed gene protein coding sequences; or mammalian cell systems (e.g. COS, CHO, BHK, 293, 3T3) harboring recombinant expression constructs containing promoters derived from the genome of mammalian cells (e.g., metallothioneine promoter) or from mammalian viruses (e.g., the adenovirus late promoter; the vaccinia virus 7.5K promoter; Cytomegalovirus Early gene promoter).

Expression of RDCVF1 or RDCVF2 by a cell from an Rdcvf1 or Rdcvf2 gene that is native to a the cell can also be performed. Methods for such expression are detailed in, e.g., U.S. Pat. Nos. 5,641,670; 5,733,761; 5,968,502; and 5,994,127, all of which are expressly incorporated by reference herein in their entirety. Cells that have been induced to express RDCVF1 or RDCVF2 by the methods of any of U.S. Pat. Nos. 5,641,670; 5,733,761; 5,968,502; and 5,994,127 can be implanted into a desired tissue in a living animal in order to increase the local concentration of RDCVF1 or RDCVF2 in the tissue.

In bacterial systems, a number of expression vectors may be advantageously selected depending upon the use intended for the differentially expressed gene protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the differentially expressed gene protein coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 264:5503-5509); and the like. PGEX vectors may also be used to express foreign polypeptides as fusion proteins with glutathione S-transferase (GST). In general, such fusion proteins are soluble and can easily be purified from lysed cells by adsorption to glutathione-asephagarose beads followed by elution in the presence of free glutathione. The PGEX vectors are designed to include thrombin or factor Xa protease cleavage sites so that the cloned target gene protein can be released from the GST moiety by using these endopeptidases.

Promoter regions can be selected from any desired gene using vectors that contain a reporter transcription unit lacking a promoter region, such as a chloramphenicol acetyl transferase ("cat") or luciferase transcription unit, downstream of restriction site or sites for introducing a candidate promoter fragment; i.e., a fragment that may contain a promoter. As is well known, introduction into the vector of a promoter-containing fragment at the restriction site upstream of the cat or luciferase gene engenders production of CAT or luciferase activity, which can be detected by standard CAT assays or luminometry. Vectors suitable to this end are well known and readily available. Three such vectors are pKK232-8, -pCM7 and pGL3 (Promega, E1751, Genebank Ass no u47295). Thus, promoters for expression of polynucleotides of the present invention include not only well known and readily available promoters, but also promoters that readily may be obtained by the foregoing technique, using a reporter gene assay.

Among known bacterial promoters suitable for expression of polynucleotides and polypeptides in accordance with the present invention are the *E. coli* lad and lacZ promoters, the T3 and T7 promoters, the T5 tac promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

In an insect system, *Autographa californica* nuclear polyhedrosis virus (AcNPV) is one of several insect systems that can be used as a vector to express foreign genes. The virus grows in *Spodoptera frugiperda* cells. The differentially expressed gene coding sequence may be cloned individually into non-essential regions (for example the polyhedrin gene) of the virus and placed under control of an AcNPV promoter (for example the polyhedrin promoter). Successful insertion of differentially expressed gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the differentially expressed gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed gene protein in infected hosts. (e.g., See Logan & Shenk, 1984, Proc. Natl. Acad. Sci. USA 81:3655-3659). Specific initiation signals may also be required for efficient translation of inserted differentially expressed gene coding sequences. These signals include the ATG initiation codon and adjacent sequences. In cases where an entire differentially expressed gene, including its own initiation codon and adjacent sequences, is inserted into the appropriate expression vector, no additional translational control signals may be needed. However, in cases where only a portion of the differentially expressed gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals (Kozack sequence) and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

Selection of appropriate vectors and promoters for expression in a host cell is a well known procedure and the requisite techniques for expression vector construction, introduction of the vector into the host and expression in the host per se are routine skills in the art.

Generally, recombinant expression vectors will include origins of replication, a promoter derived from a highly-expressed gene to direct transcription of a downstream structural sequence, and a selectable marker to permit isolation of vector containing cells after exposure to the vector.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the differentially expressed protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the differentially expressed protein. Such engineered cell lines may be particularly useful in screening and evaluation of compounds that affect the endogenous activity of the differentially expressed protein. These stable cell lines might by used as a way of cellular therapy directly or after encapsulation.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

An alternative fusion protein system allows for the ready purification of non-denatured fusion proteins expressed in human cell lines (Janknecht, et al., 1991, Proc. Natl. Acad. Sci. USA 88: 8972-8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

When used as a component in assay systems such as those described below, the differentially expressed protein may be labeled, either directly or indirectly, to facilitate detection of a complex formed between the differentially expressed protein and a test substance. Any of a variety of suitable labeling systems may be used including but not limited to radioisotopes such as $^{125}I$; enzyme labeling systems that generate a detectable calorimetric signal or light when exposed to substrate; and fluorescent labels.

Where recombinant DNA technology is used to produce the differentially expressed protein for such assay systems, it may be advantageous to engineer fusion proteins that can facilitate labeling, immobilization and/or detection.

Indirect labeling involves the use of a protein, such as a labeled antibody, which specifically binds to either a differentially expressed gene product. Such antibodies include but are not limited to polyclonal, monoclonal, chimeric, single chain, Fab fragments and fragments produced by an Fab expression library.

In another embodiment, nucleic acids comprising a sequence encoding RDCVF1 or RDCVF2 protein or functional derivative thereof, are administered to promote cone function, by way of gene therapy. Gene therapy refers to therapy performed by the administration of a nucleic acid to a subject. In this embodiment of the invention, the nucleic acid produces its encoded protein that mediates a therapeutic effect by promoting cone function.

Any of the methods for gene therapy available in the art can be used according to the present invention. Exemplary methods are described below.

In a preferred aspect, the therapeutic comprises a Rdcvf1 or Rdcvf2 nucleic acid that is part of an expression vector that expresses a RDCVF1 or RDCVF2 protein or fragment or chimeric protein thereof in a suitable host. In particular, such a nucleic acid has a promoter operably linked to the Rdcvf1 or Rdcvf2 coding region, said promoter being inducible or constitutive, and, optionally, tissue-specific. In another particular embodiment, a nucleic acid molecule is used in which the Rdcvf1 or Rdcvf2 coding sequences and any other desired sequences are flanked by regions that promote homologous recombination at a desired site in the genome, thus providing for intrachromosomal expression of the Rdcvf1 or Rdcvf2 nucleic acid (Koller and Smithies, 1989, Proc. Natl. Acad. Sci. USA 86:8932-8935; Zijlstra et al., 1989, Nature 342: 435-438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (adenovirus, adeno-associated virus and lentivirus) (see, e.g., U.S. Pat. No. 4,980,286 and others mentioned infra), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., U.S. Pat. Nos. 5,166,320; 5,728,399; 5,874,297; and 6,030,954, all of which are incorporated by reference herein in their entirety) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188; and WO 93/20221). Alternatively, the nucleic acid can be introduced intracellularly and incorporated within host cell DNA for expression, by homologous recombination (see, e.g., U.S. Pat. Nos. 5,413,923; 5,416,260; and 5,574,205; and Zijlstra et al., 1989, Nature 342:435-438).

In a specific embodiment, a viral vector that contains the Rdcvf1 or Rdcvf2 nucleic acid is used. For example, a retroviral vector can be used (see, e.g., U.S. Pat. Nos. 5,219,740; 5,604,090; and 5,834,182). These retroviral vectors have been modified to delete retroviral sequences that are not necessary for packaging of the viral genome and integration into host cell DNA. The Rdcvf1 or Rdcvf2 nucleic acid to be used in gene therapy is cloned into the vector, which facilitates delivery of the gene into a patient.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Methods for conducting adenovirus-based gene therapy are described in, e.g., U.S. Pat. Nos. 5,824,544; 5,868,040; 5,871,722; 5,880,102; 5,882,877; 5,885,808; 5,932,210; 5,981,225; 5,994,106; 5,994,132; 5,994,134; 6,001,557; and 6,033,8843, all of which are incorporated by reference herein in their entirety.

Adeno-associated virus (AAV) has also been proposed for use in gene therapy. Adeno-associated viruses are especially attractive vehicles for delivering genes to the retina. Methods for producing and utilizing AAV are described, e.g., in U.S. Pat. Nos. 5,173,414; 5,252,479; 5,552,311; 5,658,785; 5,763, 416; 5,773,289; 5,843,742; 5,869,040; 5,942,496; and 5,948, 675, all of which are incorporated by reference herein in their entirety.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient directly or after encapsulation.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a Rdcvf1 or Rdcvf2 nucleic acid is introduced into the cells such that it is expressible by the cells or their progeny, and the recombinant cells are then administered in vivo for therapeutic effect. In a specific embodiment, stem or progenitor cells are used. Any stem- and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (see, e.g., WO 94/08598), and neural stem cells (Stemple and Anderson, 1992, Cell 71:973-985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina Stem cells within the lining of the gut provide for a rapid renewal rate of this tissue. ESCs or keratinocytes obtained from the skin or lining of the gut of a patient or donor can be grown in tissue culture (Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used. Retinal stem cells (Tropepe et al., 2000, Science, 287: 2032).

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377-1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608-3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Described herein are methods for the production of antibodies capable of specifically recognizing one or more differentially expressed gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a fingerprint, target, gene in a biological sample, or, alternatively, as a method for the inhibition of abnormal target gene activity. Thus, such antibodies may be utilized as part of disease treatment methods, and/or may be used as part of diagnostic techniques whereby patients may be tested for abnormal levels of Rdcvf1 or Rdcvf2, or for the presence of abnormal forms of Rdcvf1 or Rdcvf2 by sampling the aqueous humor and/or vitreous by methods familiar to those of skill in the art (e.g. Forster, R K, Abbott, R L, Gelender, H. (1980) Management of infectious endophthalmitis Ophthalmology 87, 313-319)].

For the production of antibodies to a differentially expressed gene, various host animals may be immunized by injection with a differentially expressed protein, or a portion thereof or by DNA immunization. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with differentially expressed gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable or hypervariable region derived from a murine mAb and a human immunoglobulin constant region.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334:544-546) can be adapted to produce differentially expressed gene-single chain antibodies. Single chain antibodies are formed by linking the heavy and light chain fragments of the Fv region via an amino acid bridge, resulting in a single chain polypeptide.

Most preferably, techniques useful for the production of "humanized antibodies" can be adapted to produce antibodies to the polypeptides, fragments, derivatives, and functional equivalents disclosed herein. Such techniques are disclosed in U.S. Pat. Nos. 5,932,448; 5,693,762; 5,693,761; 5,585,089; 5,530,101; 5,910,771; 5,569,825; 5,625,126; 5,633,425; 5,789,650; 5,545,580; 5,661,016; and 5,770,429, the disclosures of all of which are incorporated by reference herein in their entirety.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275-1281) to allow rapid and easy identification of monoclonal Fab fragments with the desired specificity.

Particularly preferred, for ease of detection, is the sandwich assay, of which a number of variations exist, all of which are intended to be encompassed by the present invention.

For example, in a typical forward assay, unlabeled antibody is immobilized on a solid substrate and the sample to be tested brought into contact with the bound molecule. After a suitable period of incubation, for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the unlabeled and the labeled antibodies be an RdCVF1- or RdCVF2-specific antibody.

The most commonly used reporter molecules in this type of assay are either enzymes, fluorophore- or radionuclide-containing molecules. In the case of an enzyme immunoassay an enzyme is conjugated to the second antibody, usually by means of glutaraldehyde or periodate. As will be readily recognized, however, a wide variety of different ligation techniques exist, which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. A solution containing the appropriate substrate is then added to the tertiary complex of antibody-RdCVF1- or RdCVF2-labeled antibody. The substrate reacts with the enzyme linked to the second antibody, giving a qualitative visual signal, which may be further quantitated, usually spectrophotometrically, to give an evaluation of the amount of Rdcvf1 or Rdcvf2 which is present in the serum sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

This invention also relates to the use of polynucleotides of the present invention as diagnostic reagents. Detection of a mutated form of the gene encoding a polypeptide selected from the group consisting of the polypeptides set forth in SEQ ID NO:2, SEQ ID NO:4, SEQ ID NO:6, SEQ ID NO:8, SEQ ID NO:10, SEQ ID NO:12 and SEQ ID NO:14 which is associated with a dysfunction will provide a diagnostic tool that can add to, or define, a diagnosis of a disease, or susceptibility to a disease, which results from underexpression, over-expression or altered spatial or temporal expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents (SSCP), or by direct DNA sequencing (e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397-4401). In another embodiment, an array of oligonucleotides probes comprising the Rdcvf1 or Rdcvf2 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610-613 (1996)).

The diagnostic assays offer a process for diagnosing or determining a susceptibility to disease through detection of mutation in the Rdcvf1 or Rdcvf2 gene by the methods described. In addition, such diseases may be diagnosed by methods comprising determining from a sample derived from a subject an abnormal Rdcvf1 or Rdcvf2 expression: Expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:

(a) a polynucleotide of the present invention, preferably the nucleotide sequence encoding a polypeptide selected from the group consisting of the polypeptides set forth in SEQ ID NO:2, SEQ ID NO:4, SEQ ID NO:6, SEQ ID NO:8, SEQ ID NO:10, SEQ ID NO:12 and SEQ ID NO:14, or a fragment thereof;

(b) a nucleotide sequence complementary to that of (a);

(c) a polypeptide of the present invention, preferably the polypeptide of or a fragment thereof; or (d) an antibody to a polypeptide of the present invention, preferably to a polypeptide selected from the group consisting of the polypeptides set forth in SEQ ID NO:2, SEQ ID NO:4, SEQ ID NO:6, SEQ ID NO:8, SEQ ID NO:10, SEQ ID NO:12 and SEQ ID NO:14.

It will be appreciated that in any such kit, (a), (b), (c) or (d) may comprise a substantial component. Such a kit will be of use in diagnosing a disease or susceptibility to a disease, particularly retinitis pigmentosa, age-related macular degeneration, Bardet-Biedel syndrome, Bassen-kornzweig syndrome, best disease, choroidema, gyrate atrophy, congenital amourosis, refsun syndrome, stargardt disease and Usher syndrome. The nucleotide sequences of the present invention are also valuable for chromosome localization. The chromosomal location can be obtained by PCR on DNA prepared from a panel of hybrid cell lines (mouse-hamster). The chromosomal location of the human gene can be predicted from the location of the mouse gene by syntheny (McCarthy et al. (1997), Genome research, 7, 1153). The sequence is specifically targeted to, and can hybridize with, a particular location on an individual chromosome, including a mouse or a human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library, RetNet). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

An additional embodiment of the invention relates to the administration of a pharmaceutical composition, in conjunction with a pharmaceutically acceptable carrier, for any of the therapeutic effects discussed above. Such pharmaceutical compositions may consist of Rdcvf1 or Rdcvf2, mimetics or agonists. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions encompassed by the invention may be administered by any number of routes: e.g. Trans scleral delivery of bioreactive protein to the choroid and retina Ambati et al. (2000) Investigative Ophthalmology and Visual Science, 41, 1186. The fot mulation of topical ophthalmic preparations, including ophthalmic solutions, suspensions and ointments is well known to those skilled in the art (see Remington's Pharmaceutical Sciences, 18th Edition, Chapter 86, pages 1581-1592 Mack Publishing Company, 1990). Other modes of administration are available, including intracameral injections (which may be made directly into the anterior chamber or directly into the vitreous chamber), subconjunctival injections and retrobulbar injections, and methods and means for producing ophthalmic preparations suitable for such modes of administration are also well known.

As used in this application, "extraocular" refers to the ocular surface and the (external) space between the eyeball and the eyelid. Examples of extraocular regions include the eyelid formix or cul-de-sac, the conjunctival surface and the corneal surface. This location is external to all ocular tissue and an invasive procedure is not required to access this region. Examples of extraocular systems include inserts and "topically" applied drops, gels or ointments which may be used to deliver therapeutic material to these regions. Extraocular devices are generally easily removable, even by the patient.

The following patents disclose extraocular systems which are used to administer drugs to the extraocular regions. Higuchi et al. discloses in U.S. Pat. Nos. 3,981,303, 3,986,510 and 3,995,635, a biodegradable ocular insert which contains a drug. The insert can be made in different shapes for retention in the cul-de-sac of the eyeball, the extraocular space between the eyeball and the eyelid. Several common biocompatible polymers are disclosed as suitable for use in fabricating this device. These polymers include zinc alginate, poly (lactic acid), poly (vinyl alcohol), poly (anhydrides) and poly (glycolic acid). The patents also describe membrane coated devices with reduced permeation to the drug and hollow chambers holding the drug formulation.

Theeuwes, U.S. Pat. No. 4,217,898, discloses microporous reservoirs which are used for controlled drug delivery. These devices are placed extraocularly in the ocular cul-de-sac. Among the polymer systems of interest include poly (vinylchloride)-co-poly (vinyl acetate) copolymers. Kaufman discloses in U.S. Pat. Nos. 4,865,846 and 4,882,150 an ophthalmic drug delivery system which contains at least one bio-erodible material or ointment carrier for the conjunctival sac. The patent discloses polymer systems, such as, poly (lactide), poly (glycolide), poly (vinyl alcohol) and cross linked collagen, as suitable delivery systems.

In the presently described use of RDCVF1 or RDCVF2 protein product for the treatment of retinal disease or injury it is also advantageous that a topically applied ophthalmic formulation include an agent to promote the penetration or transport of the therapeutic agent into the eye. Such agents are known in the art. For example, Ke et al., U.S. Pat. No. 5,221,696 disclose the use of materials to enhance the penetration of ophthalmic preparations through the cornea.

Intraocular systems are those systems which are suitable for use in any tissue compartment within, between or around the tissue layers of the eye itself. These locations include subconjunctival (under the ocular mucous membrane adjacent to the eyeball), orbital (behind the eyeball), and intracameral (within the chambers of the eyeball itself). In contrast to extraocular systems, an invasive procedure consisting of injection or implantation is required to access these regions.

The following patents disclose intraocular devices. Wong, U.S. Pat. No. 4,853,224, discloses microencapsulated drugs for introduction into the chamber of the eye. Polymers which are used in this system include polyesters and polyethers. Lee, U.S. Pat. No. 4,863,457, discloses a biodegradable device which is surgically implanted intraocularly for the sustained release of therapeutic agents. The device is designed for surgical implantation under the conjunctiva (mucous membrane of the eyeball). Krezancaki, U.S. Pat. No. 4,188,373, discloses a pharmaceutical vehicle which gels at human body temperature. This vehicle is an aqueous suspension of the drug and gums or cellulose derived synthetic derivatives. Haslam et al. discloses in U.S. Pat. Nos. 4,474,751 and 4,474,752 a polymer-drug system which is liquid at room temperature and gels at body temperature. Suitable polymers used in this system include polyoxyethylene and polyoxy propylene. Davis et al. disclose in U.S. Pat. No. 5,384,333 a biodegradable injectable drug delivery polymer which provides long term drug release. The drug composition is made up of a pharmaceutically active agent in a biodegradable polymer matrix, where the polymer matrix is a solid at temperatures in the range 20.degree. to 37.degree. C. and is flowable at temperatures in the range 38.degree. to 52.degree. C. The drug delivery polymer is not limited to the delivery of soluble or liquid drug formulations. For example, the polymer can be used as a matrix for stabilizing and retaining at the site of injection drug-containing microspheres, liposomes or other particulate-bound drugs.

A particularly suitable vehicle for intraocular injection is sterile distilled water in which the RDCVF1 or RDCVF2 protein product is formulated as a sterile, isotonic solution, properly preserved. Yet another ophthalmic preparation may involve the formulation of the RDCVF1 or RDCVF2 protein product with an agent, such as injectable microspheres or liposomes, that provides for the slow or sustained release of the protein which may then be delivered as a depot injection. Other suitable means for the intraocular introduction of RDCVF1 or RDCVF2 protein product includes, implantable drug delivery devices or which contain the RDCVF1 or RDCVF2 protein product.

The ophthalmic preparations of the present invention, particularly topical preparations, may include other components, for example ophthalmically acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Sufficient tonicity enhancing agent is advantageously added so that the formulation to be instilled into the eye is hypotonic or substantially isotonic. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents include, but are not limited to, glycerin, propylene glycol and polyethylene glycol. Suitable complexing agents include caffeine, polyvinylpyrrolidone, beta-cyclodextrin or hydroxypropyl-beta-cyclodextrin. Suitable surfactants or wetting agents include, but are not limited to, sorbitan esters, polysorbates such as polysorbate 80, tromethamine, lecithin, cholesterol, tyloxapol and the like. The buffers can be conventional buffers such as borate, citrate, phosphate, bicarbonate, or Tris-HCl.

The formulation components are present in concentrations that are acceptable to the extraocular or intraocular site of administration. For example, buffers are used to maintain the composition at physiological pH or at slightly lower pH, typically within a pH range of from about 5 to about 8. Additional formulation components may include materials which provide for the prolonged ocular residence of the extraocularly administered therapeutic agent so as to maximize the topical contact and promote absorbtion. Suitable materials include polymers or gel forming materials which provide for increased viscosity of the ophthalmic preparation.

Chitosan is a particularly suitable material as an ocular release-rate controlling agent in sustained release liquid ophthalmic drug formulations (see U.S. Pat. No. 5,422,116, Yen, et. al.) The suitability of the formulations of the instant invention for controlled release (e.g., sustained and prolonged delivery) of an ophthalmic treating agent in the eye can be determined by various procedures known in the art, e.g., as described in Journal of Controlled Release, 6:367-373, 1987, as well as variations thereof.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated m aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they can be placed in an appropriate container and labeled for treatment of an indicated condition. For administration of Rdcvf1 or Rdcvf2, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example Rdcvf1 or Rdcvf2 or fragments thereof, antibodies to Rdcvf1, agonists, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. Pharmaceutical formulations suitable for oral administration of proteins are described, e.g., in U.S. Pat. Nos. 5,008,114; 5,505,962; 5,641,515; 5,681,811; 5,700,486; 5,766,633; 5,792,451; 5,853,748; 5,972,387; 5,976,569; and 6,051,561.

The following Examples illustrate the present invention, without in any way limiting the scope thereof.

EXAMPLES

1. Expression Cloning

1) Total ARN Purification from Five Weeks Normal Mouse Retinas:

The cDNA library was constructed from retinas of Five weeks old C57BL/6@N mice generally according to the method of Glissin et al (1974), Biochemistry, 13, 2633-2637. Briefly, after killing, animals were enucleated and the eyes were first placed in Phosphate Buffer Saline (PBS) supplemented with 0.1% DiEthyl PyroCarbonate (DEPC). Neural retina was quickly dissected (the retinal pigmented epithelium was omitted in this tissue preparation). Quickly after each dissection, tissues were homogenised in fresh 6 M Guanidinium Chloride. Ten retinas were pooled in 2.4 ml GC in 4 ml sterile tubes, and the tissue was disrupted completely by strong homogenisation for 1 minute at room temperature.

Messenger RNA (mRNA) Purification from Five Weeks Normal Mouse Retina:

mRNA was isolated on oligo-dT coated porous beads (Oligotex, Qiagen) under stringent conditions according to the method of Kuribayashi et al, (1988). Nucleic Acids Res. Symposium series, 19, 61-64. Briefly, 100-150 µg total mouse retina RNA were mixed with 15 µl of oligo-dT beads in Binding Buffer [10 mM Tris pH 7.5; 0.3 M NaCl; 0.1 M EDTA; 0.5% w/v Sodium Duodecyl Sulfate (SDS)] and incubated 6 minutes at 65° C. in 0.5 l becher of water, then progressively cooled to room temperature for about 3-4 hours, then centrifuged at room temperature to recover the agarose beads. They were then washed twice by incubating 10 minutes in 0.4 ml of (0.1 M Tris pH 7.5; 0.1 M NaCl; 1 mM EDTA; 0.5% w/v SDS). Bounded RNA (mRNA) were eluted in two steps with 50 µl of 70° C.-warmed RNAse-free water, precipitated with 10 µl Sodium Acetate pH 5.2 and 0.25 ml ethanol and incubated 12 hours at −70° C. mRNA were collected by centrifugation (1 hour at 15.000 rpm, followed by two washes with 70% ethanol) and resuspended in 20 µl of RNAse-free water. mRNA concentration was measured at 260 nm and the absence of rRNA contaminations was checked by gel electrophoresis under denaturating condition as above.

cDNA Synthesis:

was carried out according to the method of Okayama and Berg, (1982), Mol Cell Biol., 2, 161-170. First strand synthesis was primed with 2.5 µg of NotI adaptor oligonucleotide (5'TGTTACCAATCTGAAGTGGGAGCGGCCGACAA(T)$_{18}$3' (SEQ ID NO: 28)) and incubated for 2 hours with 50 units of modified Moloney Murine Leukaemia virus (M-MLV) reverse transcriptase (Superscript II, Life Technology) under the conditions recommended by the supplier. For second strand synthesis, reaction was incubated 4 hours at 14° C. with 4 units of RNAseH and 100 units of DNA polymerase I in SS Buffer [40 mM Tris pH 7.2; 85 mM Potassium Chloride; 4.4 mM Magnesium chloride; 3 mM DTT; 5 µg/ml Bovin Serum Albumin (BSA)] in a final volume of 0.25 ml. EcoRI adapters (5'-OHAATTCGGCACGAGG 3'-OH (SEQ ID NO: 29)/3'-OH GCCGTGCTCC5'-PO$_4$ (SEQ ID NO: 30)) were ligated at both ends of double strand cDNA in 14 hours at 16° C. using 40 units of T4 DNA ligase (Promega, Madison, USA) in a total volume of 20 µl under the conditions recommended by the supplier. The products of this reaction are dscDNA that have an EcoRI half site in 5' and NotI half site in 3' that can be oriented in the cloning vector.

Ligation of dscDNA in pcDNA3:

was performed according to Maniatis T. (1992), Molecular cloning: a laboratory manual, 2nd ed., using 10 µg of pcDNA3 plasmid (Invitrogen) prepared by cutting with EcoRI and NotI (Promega, Madison, USA) under the conditions specified by the supplier.

Propagation of Recombinant Clones:

was performed generally according to the method of Birnboim et al (1979), Nucleic Acids Res., 7, 1513-1523. Briefly, In order to make pools of 100 primary clones, we slightly modified the XL1 Gold (Strategene) transformation protocol (provided by Stratagene) as followed. After incubation in growth medium, the transformation reaction was brought to 20% (vol./vol.) glycerol and 8% (vol./vol.) horse serum albumin (HAS, Life Technologies). HAS and glycerol prevent death followed freezing thawing. A titration was done by platting on agar plates (100 µg/ml ampicillin) increasing volume of each transformation reaction to calculate the volume giving 100 colonies, while the bulk transformation reaction was stored at −80° C. Recombinant plasmids from the library were purified by 96 at once. In order to prepare 96 pools of 100 clones, the calculated volume corresponding to 100 clones was platted on agar and grown 20 hours at 37° C. The DNA was purified directly from colonies striped from agar plates. A stock of each culture at 23% glycerol was stored at −80° C. The DNA was purified using Qiawell ultra (Qiagen,) using a protocol recommended by the supplier. Typically, 10 µg of purified plasmid were obtained, the concentration of each preparation was measured using optical density at 260 nm. To sub-divide selected pools of 100 into pools of 10, 50 µl of a 1/250.000 dilution of the glycerol stock from the original pool was plate on an agar plate at 100 µg/ml ampicillin. After growth 16 hours at 37° C., individual 160 colonies were replicated on 16 agar plates (10 per plate) and grown 16 hours at 37° C. The 10 colonies from each plate were harvested and grown in liquid medium [Luria Broth (LB), 100 ug/ml ampicillin] for 3 hours at 37° C. A stock of these cultures at 30% glycerol was stored at −80° C. Plasmid DNA was prepared as before. To divide sub-pools of 10 into individual clones, 50 µl of a 1/250.000 dilution of the glycerol stock of the sub-pools of 10 was plated onto agar plate with 100 µg/ml ampicillin. After growth 16 hours at 37° C., 16 individual colonies were picked and grown 16 hours in 2 ml LB 100 µg/ml ampicillin. A stock of these cultures at 30% glycerol was stored at −80° C. Plasmid DNA was prepared as before.

Transient Transfection in Cos-1 Cells:

was performed using the method of Chen and Okayama, (1987). High-efficiency transformation of mammalian cells by plasmid DNA (Mol Cell Biol., 7, 2745-2752).

Chick Embryo Retinal Cultures:

The protocol was adapted from Adler and Hatlee [(1989) Science, 243, 391]. Chick embryonic retina (6 days in ovo) is dissociated and plated in monolayer culture. Under these culture conditions with the absence of differentiation signals, cones represent 60-80% of cells. We have produced polyclonal antibodies into rabbit against visinin (a chicken cone marker, Genbank accession number M84729) and verified that the proportion of cones in our culture is of 60-80%. The simple environment of our model (chemically defined medium, absence of cell to cell contacts) in addition to the ease and speed of the method make it a very appropriate system to study trophic factors involved in cone survival. Briefly, Retinas from embryos issued from a control isolate of progenitors, are dissected after six days of development in ovo, cells dissociated and plated at low density ($10^5$ cells/cm$^2$). During ten days cell viability (60-80% cones) was followed using LIVE/DEAD assay (Molecular probes, Eugene, USA) an assay that quantifies live and dead cells. The number of cells alive decreases down to 8% of initial cells number after seven days in culture in chemically defined medium. When performed in the presence of conditioned media from COS 1 cells transfected with pools of clones from the library, live cells are counted after seven days in vitro.

Chicken progenitors (strain 657 red label) were maintained in a separated compartment for the purpose of this experiment in a hatching facility 25 km from the laboratory. Fertilized eggs obtained naturally were collected weekly, and maintained at 17° C. (their biological zero) in the laboratory after hatching. Daily, 5 eggs are incubated for 24 hours at 20° C. then 136 hours at 37° C. with intermittent reversion of the inclination of the eggs in a humidified chamber. The day of the culture, eggs surface are washed with Mucocit-A then broken, the chicken embryos are transferred in PBS. The stage of development of the each embryo is verified be the 29$^{th}$ by visual comparison to Hamburger and Hamilton (1951), in (Essential Development Biology, Stem and Holland Ed.). Two of the embryos were chosen and enucleated, the eyes transferred in CO$_2$-independent medium (Life technologies). Retinas were dissected and transferred in Ringer buffer and washed twice. Retinas are cut in small pieces and treated 20 minutes at 37° C. with a solution of trypsin (0.25% w/v). The reaction is stopped by addition of culture media (M199, Life Technologies) supplemented with 10% inactivated FCS. The cell suspension is treated for few minutes in 25 µl of DNAse I (1 mg/ml, Sigma). The cell suspension is then washed twice in Chemical Defined Culture Media [CDCM, equal volumes of DMEM and M199 media (Life Technologies) and AB with Supplements (5 µg/ml Insulin; 5 µg/ml Transferring; 64 nM Progesterone; 0.1 mM Putrescin; 5 ng/ml Selenium; 3 mM Taurine; 2.7 µM Cytidine 5'-diphosphoethanolamine; 5.2 µM Cytidine 5'-diphosphocholine, 0.2 µg/ml Hydrocortisone; 30 nM 3,3'-5-triiodo-L-thyronine; 1 mM Sodium Pyruvate), 0.3 µM Prostaglandin D$_2$; 0.1 mg/ml linoleic acid] in order to remove the FCS. The concentration of cells stained with trypan blue is measured with Mallassez' cell and brought to two concentrations (5.6 and 1.12 $10^5$ cells/ml) corresponding to the two plating densities (2 and 4 $10^5$ cells/cm$^2$).

Conditioned media from Cos-1 transfected cells are thaw on ice and 50 µl transferred to two 96 wells tissue culture treated black plate (Corning Costar) that have been coated a solution of 100 µg/ml Poly-L-lysine (Sigma) according the plan:

First Round of Screening:

| 1  | 1  | 1  | 1  | 2  | C  | 2  | 2  | 2  | 3  | 3  | P  |
|----|----|----|----|----|----|----|----|----|----|----|----|
| C  | 3  | 3  | 4  | 4  | 4  | C  | 4  | 5  | 5  | 5  | 5  |
| 6  | C  | 6  | 6  | 6  | 7  | 7  | C  | 7  | 7  | 8  | 8  |
| 8  | 8  | C  | 9  | 9  | 9  | 9  | 10 | C  | 10 | 10 | 10 |
| 11 | 11 | 11 | C  | 11 | 12 | 12 | 12 | 12 | C  | 13 | 13 |
| 13 | 13 | 14 | 14 | C  | 14 | 14 | 15 | 15 | 15 | C  | 15 |
| 16 | 16 | 16 | 16 | 17 | C  | 17 | 17 | 17 | 18 | 18 | C  |
| 18 | 18 | 19 | 19 | 19 | 19 | P  | 20 | 20 | 20 | C  | 20 |

Where numbers refer to no of pools of 100 clones, C to conditioned media from Cos-1 cells transfected with the empty vector (pcDNA3) and P a positive control (conditioned media transfected with pcDNA-mouseGDNF.

Second and Third Round of Screening:

| x.(y).01 | x.(y).01 | x.(y).01 | x.(y).01 | x.(y).02 | C        | x.(y).02 | x.(y).02 | x.(y).02 | x.(y).03 | x.(y).03 | P        |
| C        | x.(y).03 | x.(y).03 | x.(y).04 | x.(y).04 | x.(y).04 | C        | x.(y).04 | x.(y).05 | x.(y).05 | x.(y).05 | x.(y).05 |
| x.(y).06 | C        | x.(y).06 | x.(y).06 | x.(y).06 | x.(y).07 | x.(y).07 | C        | x.(y).07 | x.(y).07 | x.(y).08 | x.(y).08 |
| x.(y).08 | x.(y).08 | C        | x.(y).09 | x.(y).09 | x.(y).09 | x.(y).09 | x.(y).10 | C        | x.(y).10 | x.(y).10 | x.(y).10 |
| x.(y).11 | x.(y).11 | x.(y).11 | C        | x.(y).11 | x.(y).12 | x.(y).12 | x.(y).12 | x.(y).12 | C        | x.(y).13 | x.(y).13 |
| x.(y).13 | x.(y).13 | x.(y).14 | x.(y).14 | C        | x.(y).14 | x.(y).14 | x.(y).15 | x.(y).15 | x.(y).15 | C        | x.(y).15 |
| x.(y).16 | x.(y).16 | x.(y).16 | x.(y).16 | x.(y)    | C        | x.(y)    | x.(y)    | x.(y)    | C57      | C57      | C        |
| C57      | C57      | C3H      | C3H      | C3H      | C3H      | P        | 0        | 0        | 0        | C        | 0        |

Where x (second round) and y (third round) represent the no of the pools selected in the first and second round respectively. 01 to 16 represent the sub-pools used. x(y) represents the parental pool from which the 16 pools derived. C is as is first round. P was modified as pCMVScript-CNTF in the second round and progressively to pcDNA-939.09.08 in the third round. 0 represents chick cone cells in CDCM media only. C57 and C3H, conditioned media from explants of retinas prepared as described in (preparing conditioned media from explants of mouse retinas) from C57BL/6@N and C3H/He@N mouse retinas aged of 5 weeks respectively.

50 µl of cell suspensions corresponding to two densities (2 and 4 $10^5$ cells/cm$^2$) were added to the well of the two 96 wells plates filled conditioned media with a 8 channel motorized pipette (Biohit) in order to minimized experimental errors. Cells were incubated for 7 days at 37° C. in 5% CO$_2$.

Preparing Conditioned Media from Explants of Mouse Retinas:

The second and third round screening included positive controls adapted from Mohand-Saïd et al. (1998). Five weeks aged mouse 5C57BL/6@N (wild type) and C3H/He@N (rdl) were sacrificed and enucleated. Two retinas were dissected and incubated in 24 hours at 37° C. in 5% CO$_2$ in 1.5 ml of CDCM in 12 wells plates. Conditioned media were recovered and concentrated by a factor 40 by ultra-filtration on Vivaspin (Sartorius, cutting point 10 kDa). Conditioned media were frizzed in liquid nitrogen and stored in aliquots at −20° C. before used. The day of use, conditioned media were thawed on ice, diluted 10 times in CDCM and sterilized by filtration on 0.22 µm filter (Acrodisk 13, Gelman Sciences).

Functional Assay, Live/Dead Assay:

The functional assay is based on the number of chicken retinal cells alive after 7 days incubation in vitro. We used Live/Dead assay kit (Molecular probes, Eugene, USA) that is based on the use of two fluorogenic dyes (Calcein AM and Ethidium dimer) that stain live and dead cells respectively. A cell that is alive processes a metabolic activity (here an esterase activity) that coverts the substrate (Calcein AM) in its fluorescent product emitting at 520 nm. The membrane permeability of a dead cell is altered and permits the DNA staining of the nucleus by Ethidium dimmer emitting at 635 nm. A cell is alive: emitting at 520 nm after excitation at 485 nM, or dead: emitting at 635 nm after excitation at 520 nm. Using epifluorescence microscopy, the two types of fluorescent cells can be visualized separately. After 7 days in vitro, cells were incubated for 30 minutes at room temperature in the dark with 2.7 µM Calcein-AM and 0.3 mM Ethidium dimer.

Image Acquisition:

Briefly, image acquisition consisted of autofocusing each well, automatic cell counting in two fluorescence's followed by processing of the raw data using specialist software e.g. Metamorph (Universal Imaging Corporation, West Chester, USA) to obtain digitalised pictures of each well of the plate. We used a inverted microscope (Nikon TE 200) equipped with a mercury epifluorescent lamp with two excitation filters 485 and 520 nm, two emission filters 520 and 635 nm, an object (×10), a computer driven motorized platine (Multicontrol 2000, Martzauzer and a CCD camera (Cohu).

To record the plate, it is positioned on the motorised platine, and the focus done manually on the first well and this plane is recorded (z origin). The threshold of the image dead and live is set from the first well. The centre of the first well is adjusted using white light by aligning manually the bottom of the first well to the bottom of the image on the computer monitor, then by aligning the extreme right of the first well to the right of the image on the computer screen and to record the two positions. The centre of the first well is calculated and gives the position of the centre of each well of the plate. We have noticed in the development process that there is a slight higher density of cells at the edge of the well and excluded the edge from the acquisitions. It is important that the image from each well be centred perfectly in order to avoid any misleading results. When set-up, the first scan of the plate executes a recording of dead cells. The dead cells density is the less variable under these conditions. The application executes an auto focusing by taking images at different focal plans and choosing the brightest one, the right focus. This z position is stored and platine executes programmed movements in the x and y axes taking a total of 4 images that when reconstituted in one image represents 2/3 of the surface of the well. A pile of images from the focus plans is stored for control. The platine executes an auto focusing and four acquisitions for each well of the plate starting by wells A1 to A12, then B12 to B1, C1 to C12 etc. . . . At the end, the platine moves outside the plate in order to overexpose the last well (H1). The scanning of dead cells takes 30 minutes. The second scan (live cells) is executed after switching the filter. This second scan is using the recorded z positions of each well from the dead scan. Four images are taken from each well as for dead cells. At the end of the second scan (22 minutes) dead and live reconstituted images are stored in a file that is named automatically with the date of the day. Cells numbers (dead and line) are counted automatically with pre-set morphometric parameters (average) and displayed on the computer monitor in order to check if the experiment is correct. It is important to check on a daily basis that the number of cells alive is not too high. We have observed that if plated at too important density, the chicken retinal cells survived longer most likely by producing their own survival factor. We screened cells in the absence of this effect. Before scanning the second plate (same experiment with twice density of cells plated), we add an a at the end of the name of the log file from the first plate. Images of each experiment were stored on CD-rom. We have generated a library of more than 250 CD-rom.

Cells Counting and Selection of the Pools:

The cells numbers (live and dead) were counted using images of each experiment stored on CD-rom. The log file from an experiment was first loaded on a computer (counting off-line) and opened using Metamorph software. In a first step, the images corresponding to the 14 wells C (conditioned media from Cos-1 cells transfected with the empty vector) are opened. After adjusting the threshold of the image, the command Integrated Morphometry Analysis is used to measure the distribution of the areas between 10 and 250 of the object (number of live cells for each total area) for these control wells. The distribution follows a Gaussian curve with the maximal number of objects corresponding to an isolated cell. This standard value (SV) is then used to calculate the value of the area above which an object will be counted as two cells (standard object cut, SOC) through our empirical function: SOC=29/20.74 SV. The SOC value of each individual plate is used to count the number of live cells of the plate. These numbers are then transferred into a excel table.

For the first round of screening, the value were plotted for each pool as fold difference (increase or decrease live cells numbers) versus the average of the 14 control wells+the standard deviation. In order to redress the variations coming from the position difference within the plate, we calculated the average of the fold difference individually between the 80 wells corresponding to positions where the pools are tested and the 14 wells control for 200 independent plates. In average, the differences observed are due only to position difference and cells numbers were corrected with this coefficient. In order to discriminate in more stringent way the pools to be selected, the live cells counts were plotted as fold difference versus as control all values not exceeding 1.3 but exceeding 0.4. In this manner, all pools were fold difference versus the 14 wells corresponding to empty vector are in the interval of 0.4 to 1.3 are considered as having no effect and used as control. After correction, the fold difference versus control of the two plates was multiplied and the result sorted by decreasing fold difference. The pools on the top of that list were further checked by visual inspection of the graph corresponding to the 20 pools of the experiment (both plates) and of the images of live and dead cells to avoid to screen misleading pools.

For the second and third round, the plates screening for sub-pools include additional control. We prepared conditioned media from retina explants of 5 weeks of age. We selected experiments where positive effects were recorded for retina explants from C57BL/6@N and dismissed the others. The results were plotted as fold difference versus the 14 control wells, no recalculation of the control was made. The fold difference versus control of the two plates was multiplied and the results were sorted by decreasing fold difference for the 16 sub-pools.

Isolated cDNA were sequenced using T7 primer (5'GTAATACGACTCACTATAGGGC 3' (SEQ ID NO: 31)) on a capillary sequencer (CEQ2000, Beckman Coulter). DNA sequence was compared to databases using Basic Local Alignment Search Tool (BLAST).

Identification of Rdcvf2 and Human Homologues:

Using the Rdcvf1 sequence (the nucleotide sequence encoding the polypeptides set forth in SEQ ID NO:2 or SEQ ID NO:4) and BLAST, homologous murine and human polypeptides were identified (FIG. 8). EST clones with homology to mouse RdCVF2 (GenBank Accession No: bc016199) were identified: GenBank Accession Nos: be552141, bi517442, bg707818, bi603812, ai433287, be088414, bg297383, bg297304 (see also FIG. 12). EST clones with homology to mouse Rdcvf1 (SEQ ID NO:1) were identified: GenBank Accession Nos: bg299078, ai716631, bg294111, be108041, bg395178 (see also FIG. 13).

Real-Time RT-PCR Analysis of Rdcvf1 Rdcvf1 Expression

The retinal expression of Rdcvf1 by mouse C57BL/6@N and C3H/He@N aged as well as congenic C3H (+/+ and rd/rd) of 5 weeks is studied using real-time RT-PCR on a lightcycler (Roche) with sybergreen PCR kit (Roche). cDNAs are produced by priming with a random hexamer oligonucleotide (pdN6, Amersham), M-MLV reverse transcriptase (superscript II, Life Technologies) and total RNA from mouse retina prepared as in 1). cDNAs are normalized using a ubiquitous messenger Glucose-6-Phosphate DeHydrogenase (G6PDH). 0.2 µl of first strand cDNAs synthesis (an equivalent of 10 ng of total RNA) is amplified with 2 µM of the oligonucleotides of SEQ ID NO:24 and SEQ ID NO:25 in triple in a total volume of 25 µl using the following program: 30 seconds at 95° C., and 35 cycles of a sequence (1 second at 95° C., 18 seconds at 55° C., 10 seconds at 72° C.), The analysis (FIG. 16) shows that Rdcvf1 expression decreases after rod degeneration in the rd1 mouse (C3H/He@N). Rdcvf1 was also shown to be directly expressed by photoreceptors by real-time RT-PCR using RNA prepared from outer layer of the retina by vibratome sectioning.

Products were checked by agarose gel electrophoresis. Similar results are obtained with another pair of Rdcvf1 specific primers. As a positive control, the expression of rod arrestin (Ass no M24086) is monitored in the same conditions with primers

```
(5'CTATTACGTCAAGCCTGTAGCC 3'   (SEQ ID NO: 32)
and

5'CATCCTCATCTTTCTTCCCTTC 3'   (SEQ ID NO: 33)).
```

Confirmation that Rdcvf1 is the cone protective factor can be obtained by adding a suitable amount of Rdcvf1 to a retinal explant of 5 week old rd1 mouse (C3H/He@N). What is a suitable amount can be arrived at by some initial titration experiments. Compare with appropriate controls after 7 days cone survival will be increased.

RT-PCR Analysis of Rdcvf2

RT-PCR for Rdcvf2 expression was carried out using primers

```
5'GCCAGCGTTTTCTGCCTTTTAC 3'      (SEQ ID NO: 34)
and

5'AAGCCCTGCCTGCTCTAACATC 3'.     (SEQ ID NO: 35)
```

The analysis shows that RdCVF2 is expressed in a rod-dependent manner and that Rdcvf2 expression is not restricted to the retina, but that also other neuronal cells express Rdcvf2 (FIG. 17), whereas the expression of Rdcvf1 seems to be restricted to retinal cells.

Live/Death Assays of Rdcvf1 or Rdcvf2

COS-1 cells are transfected with a suitable expression vector carrying the Rdcvf1 or Rdcvf2 under control of a inducible promoter. Control cells are transfected with the empty vector. The cells are incubated for a suitable period of time upon induction of Rdcvf1 or Rdcvf2 expression. Subsequently, the number of surviving cone cells incubated with conditioned media from COS-1 cells transfected with Rdcvf1 or Rdcvf2 and the number of surviving control cells are counted according to the above described method. The cells expressing Rdcvf1 or Rdcvf2 show a significantly higher amount of surviving cells.

Rod Specific Factor

Real-time RT-PCR analysis, carried out under standard conditions, of the expression of rod arrestin (control) and Rdcvf1 in 5 weeks retinal explants from C57BL/6@N 5 weeks and C3H/HE@N, using the primers:

```
SEQ ID NO: 24:     5' TCTATGTGTCCCAGGACCCTACAG 3'

SEQ ID NO: 25:     5 TTTATGCACAAGTAGTACCAGGACAG 3'
``` demonstrates that RdCVF1 is expressed only in the presence of rods (Rod-derived CVF1).

Production of Polyclonal Antibodies:

Polyclonal antibodies are prepared by injecting a Gluthation-S-Transferase (GST) purified fusion protein (GST-Rdcvf1) as well as from mouse RdCVF1 peptide sequence amino acids 11 to 32 from SEQ ID NO2 (Ab no 2) and peptide sequence amino acids 79 to 96 from SEQ ID NO2 (Ab no 3) into rabbit. The fusion construct pGST-Rdcvf1 is prepared by amplification with oligonucleotides of SEQ ID NO:26 and SEQ ID NO:27 using peDNA-Rdcvf1 as template under standard conditions. The Open Reading Frame (ORF) of Rdcvf1 is cloned in frame into pGex2TK (Pharmacia) between the BamHI and EcoRI restriction sites, and transformed into E. coli [BL21 (DE3) pLysS, Promega] by standard procedure. A single colony is grown in 3 liters of LB liquid media with 100 µg/ml ampicillin at 30° C. and protein production is induced by addition of 1 µg/ml isopropylthio-β-D-galactoside (IPTG) and continued for 5 hours at 30° C. Cells are harvested, lysed be sonication and purified onto gluthation sepharose under standard protocol. The fusion protein is eluted with 10 mM reduced gluthation at room temperature. The Eluted protein is dialyzed into PBS before injection to rabbits. Protein purity is monitored by polyacrylamide gel electrophoresis. Two rabbits are immunized by intradermic injection at 80 sites of 100 µg of purified GST-Rdcvf1. Serum is harvested after 8 weeks.

What is claimed is:

1. A method of treating retinitis pigmentosa in a subject, the method comprising directly administering to the retinal cells of the subject a pharmaceutical composition comprising:
   a) a viral vector comprising a nucleic acid, wherein the nucleic acid comprises a nucleotide sequence encoding a Rod-Derived Cone Viability Factor 1 (RDCVF1) or a Rod-Derived Cone Viability Factor 2 (RDCVF2) polypeptide and wherein the nucleotide sequence is operably linked to an expression control sequence, and
   b) a pharmaceutically acceptable carrier,
wherein expression of the RDCVF1 or RDCVF2 polypeptide in the retinal cells of the subject treats the retinitis pigmentosa.

2. The method of claim 1, wherein the viral vector is an adeno-associated virus vector.

3. The method of claim 1, wherein the viral vector is an adenovirus vector.

4. The method of claim 1, wherein the expression control sequence is an inducible promoter.

5. The method of claim 1, wherein the expression control sequence is a constitutive promoter.

6. The method of claim 1, wherein the expression control sequence is a tissue specific promoter.

7. The method of claim 1, wherein the polypeptide is a human RDCVF1 polypeptide.

8. The method of claim 7, wherein the polypeptide is a long form of the human RDCVF1 polypeptide.

9. The method of claim 7, wherein the polypeptide is a short form of the human RDCVF1 polypeptide.

10. The method of claim 1, wherein the polypeptide is a human RDCVF2 polypeptide.

11. The method of claim 10, wherein the polypeptide is a long form of the human RDCVF2 polypeptide.

12. The method of claim 10, wherein the polypeptide is a short form of the human RDCVF2 polypeptide.

13. The method of claim 1, wherein the polypeptide comprises the amino acid sequence of SEQ ID NO:6.

14. The method of claim 1, wherein the polypeptide comprises the amino acid sequence of SEQ ID NO:8.

15. The method of claim 1, wherein the polypeptide comprises the amino acid sequence of SEQ ID NO:14.

* * * * *

SEQUENCE LISTING

```
<160> NUMBER OF SEQ ID NOS: 38

<210> SEQ ID NO 1
<211> LENGTH: 468
<212> TYPE: DNA
<213> ORGANISM: Mus musculus
<220> FEATURE:
<221> NAME/KEY: CDS
<222> LOCATION: (45)..(374)

<400> SEQUENCE: 1
```

```
atcgatccc tctctgggtc cccagctcct tgcatactgc tacc atg gca tct ctc        56
                                              Met Ala Ser Leu
                                              1 ttc tct gga cgc atc ttg atc agg aac aac agc gac cag gat gaa gtg        104
Phe Ser Gly Arg Ile Leu Ile Arg Asn Asn Ser Asp Gln Asp Glu Val
5                   10                  15                  20 gag aca gag gca gag ctg agc cgt agg tta gag aat cgt ctg gtg ttg        152
Glu Thr Glu Ala Glu Leu Ser Arg Arg Leu Glu Asn Arg Leu Val Leu
                25                  30                  35 ctg ttc ttc ggc gcc ggc gcc tgt ccc cag tgc cag gcc ttt gcc cca        200
Leu Phe Phe Gly Ala Gly Ala Cys Pro Gln Cys Gln Ala Phe Ala Pro
            40                  45                  50 gtc ctc aaa gac ttc ttc gtg cgg ctc act gac gag ttc tac gtg ctg        248
Val Leu Lys Asp Phe Phe Val Arg Leu Thr Asp Glu Phe Tyr Val Leu
        55                  60                  65 cgg gca gca cag ctg gcc ctg gtc tat gtg tcc cag gac cct aca gag        296
Arg Ala Ala Gln Leu Ala Leu Val Tyr Val Ser Gln Asp Pro Thr Glu
    70                  75                  80 gag caa cag gac ctc ttc ctc agg gac atg cct gaa aaa tgg ctc ttc        344
Glu Gln Gln Asp Leu Phe Leu Arg Asp Met Pro Glu Lys Trp Leu Phe
85                  90                  95                  100 ctg ccg ttc cat gat gaa ctg agg agg tga ggccccaggg aagaccaggg         394
Leu Pro Phe His Asp Glu Leu Arg Arg
                105 agggcttcct ggagaaggca tttccctgga ggtttactgt cctggtacta cttgtgcata     454 aagaggtatt cctc                                                       468

<210> SEQ ID NO 2
<211> LENGTH: 109
<212> TYPE: PRT
<213> ORGANISM: Mus musculus

<400> SEQUENCE: 2

Met Ala Ser Leu Phe Ser Gly Arg Ile Leu Ile Arg Asn Asn Ser Asp
1               5                   10                  15

Gln Asp Glu Val Glu Thr Glu Ala Glu Leu Ser Arg Arg Leu Glu Asn
            20                  25                  30

Arg Leu Val Leu Leu Phe Phe Gly Ala Gly Ala Cys Pro Gln Cys Gln
        35                  40                  45

Ala Phe Ala Pro Val Leu Lys Asp Phe Phe Val Arg Leu Thr Asp Glu
    50                  55                  60

Phe Tyr Val Leu Arg Ala Ala Gln Leu Ala Leu Val Tyr Val Ser Gln
65                  70                  75                  80

Asp Pro Thr Glu Glu Gln Gln Asp Leu Phe Leu Arg Asp Met Pro Glu
                85                  90                  95

Lys Trp Leu Phe Leu Pro Phe His Asp Glu Leu Arg Arg
            100                 105

<210> SEQ ID NO 3
<211> LENGTH: 764
<212> TYPE: DNA
<213> ORGANISM: Mus musculus
<220> FEATURE:
<221> NAME/KEY: CDS
<222> LOCATION: (26)..(676)

<400> SEQUENCE: 3
ccccagctcc ttgcatactg ctacc atg gca tct ctc ttc tct gga cgc atc       52
                           Met Ala Ser Leu Phe Ser Gly Arg Ile
```

|  |  |  |  |  |  |  |  |  |  |  |  |  |  |  |  |
|---|---|---|---|---|---|---|---|---|---|---|---|---|---|---|---|
| ttg | atc | agg | aac | aac | agc | gac | cag | gat | gaa | gtg | gag | aca | gag | gca | gag | 100
| Leu | Ile | Arg | Asn | Asn | Ser | Asp | Gln | Asp | Glu | Val | Glu | Thr | Glu | Ala | Glu |
| 10 |  |  |  | 15 |  |  |  |  | 20 |  |  |  |  | 25 |  |

```
                 1               5
ttg atc agg aac aac agc gac cag gat gaa gtg gag aca gag gca gag     100
Leu Ile Arg Asn Asn Ser Asp Gln Asp Glu Val Glu Thr Glu Ala Glu
 10              15                  20                  25 ctg agc cgt agg tta gag aat cgt ctg gtg ttg ctg ttc ttc ggc gcc     148
Leu Ser Arg Arg Leu Glu Asn Arg Leu Val Leu Leu Phe Phe Gly Ala
             30                  35                  40 ggc gcc tgt ccc cag tgc cag gcc ttt gcc cca gtc ctc aaa gac ttc     196
Gly Ala Cys Pro Gln Cys Gln Ala Phe Ala Pro Val Leu Lys Asp Phe
         45                  50                  55 ttc gtg cgg ctc act gac gag ttc tac gtg ctg cgg gca gca cag ctg     244
Phe Val Arg Leu Thr Asp Glu Phe Tyr Val Leu Arg Ala Ala Gln Leu
     60                  65                  70 gcc ctg gtc tat gtg tcc cag gac cct aca gag gag caa cag gac ctc     292
Ala Leu Val Tyr Val Ser Gln Asp Pro Thr Glu Glu Gln Gln Asp Leu
 75                  80                  85 ttc ctc agg gac atg cct gaa aaa tgg ctc ttc ctg ccg ttc cat gat     340
Phe Leu Arg Asp Met Pro Glu Lys Trp Leu Phe Leu Pro Phe His Asp
 90                  95                 100                 105 gaa ctg agg agg gac ctc ggg cgc cag ttc tct gtc cgt caa ctg cca     388
Glu Leu Arg Arg Asp Leu Gly Arg Gln Phe Ser Val Arg Gln Leu Pro
             110                 115                 120 gcg gtt gtg gta ctt aag cct ggt ggg gac gtg ctg aca agc gac gcc     436
Ala Val Val Val Leu Lys Pro Gly Gly Asp Val Leu Thr Ser Asp Ala
         125                 130                 135 acg gag gag atc cag cgt ctg gga ccc gcc tgc ttt gcc aac tgg cag     484
Thr Glu Glu Ile Gln Arg Leu Gly Pro Ala Cys Phe Ala Asn Trp Gln
     140                 145                 150 gag gcc gca gag ctc ctg gac cgc agc ttc ctg caa ccg gag gat ttg     532
Glu Ala Ala Glu Leu Leu Asp Arg Ser Phe Leu Gln Pro Glu Asp Leu
 155                 160                 165 gat gag cct gcg cgg cgc agc atc acc gag cct ctg cgc cgt cgc aag     580
Asp Glu Pro Ala Arg Arg Ser Ile Thr Glu Pro Leu Arg Arg Arg Lys
170                 175                 180                 185 tac cga gta gac cgg gat gtc ggc ggg agc ggg gcg aaa cgg cgc gac     628
Tyr Arg Val Asp Arg Asp Val Gly Gly Ser Gly Ala Lys Arg Arg Asp
             190                 195                 200 tct ggt gaa ccc cag ggg gac gcg ggt aca agg gcg gag ctc tgg tga     676
Ser Gly Glu Pro Gln Gly Asp Ala Gly Thr Arg Ala Glu Leu Trp
         205                 210                 215 ctcccagggt aggagtgggg accggagctc tggtgacacc aaagtaccgg tgcacgaccg     736
aggttgatga ccctcccgaa ggaaccgg                                       764

<210> SEQ ID NO 4
<211> LENGTH: 216
<212> TYPE: PRT
<213> ORGANISM: Mus musculus

<400> SEQUENCE: 4

Met Ala Ser Leu Phe Ser Gly Arg Ile Leu Ile Arg Asn Asn Ser Asp
 1               5                  10                  15

Gln Asp Glu Val Glu Thr Glu Ala Glu Leu Ser Arg Arg Leu Glu Asn
             20                  25                  30

Arg Leu Val Leu Leu Phe Phe Gly Ala Gly Ala Cys Pro Gln Cys Gln
         35                  40                  45

Ala Phe Ala Pro Val Leu Lys Asp Phe Phe Val Arg Leu Thr Asp Glu
     50                  55                  60

Phe Tyr Val Leu Arg Ala Ala Gln Leu Ala Leu Val Tyr Val Ser Gln
```

```
                    65                  70                  75                  80
Asp Pro Thr Glu Glu Gln Gln Asp Leu Phe Leu Arg Asp Met Pro Glu
                        85                  90                  95

Lys Trp Leu Phe Leu Pro Phe His Asp Glu Leu Arg Arg Asp Leu Gly
                100                 105                 110

Arg Gln Phe Ser Val Arg Gln Leu Pro Ala Val Val Leu Lys Pro
            115                 120                 125

Gly Gly Asp Val Leu Thr Ser Asp Ala Thr Glu Glu Ile Gln Arg Leu
        130                 135                 140

Gly Pro Ala Cys Phe Ala Asn Trp Gln Glu Ala Ala Glu Leu Leu Asp
145                 150                 155                 160

Arg Ser Phe Leu Gln Pro Glu Asp Leu Asp Glu Pro Ala Arg Arg Ser
                165                 170                 175

Ile Thr Glu Pro Leu Arg Arg Lys Tyr Arg Val Asp Arg Asp Val
            180                 185                 190

Gly Gly Ser Gly Ala Lys Arg Arg Asp Ser Gly Glu Pro Gln Gly Asp
        195                 200                 205

Ala Gly Thr Arg Ala Glu Leu Trp
    210                 215

<210> SEQ ID NO 5
<211> LENGTH: 353
<212> TYPE: DNA
<213> ORGANISM: Homo sapiens
<220> FEATURE:
<221> NAME/KEY: CDS
<222> LOCATION: (24)..(353)

<400> SEQUENCE: 5
cccagcaccc aacccaggtt acc atg gcc tcc ctg ttc tct ggc cgc atc ctg        53
                        Met Ala Ser Leu Phe Ser Gly Arg Ile Leu
                          1               5                  10 atc cgc aac aat agc gac cag gac gag ctg gat acg gag gct gag gtc        101
Ile Arg Asn Asn Ser Asp Gln Asp Glu Leu Asp Thr Glu Ala Glu Val
             15                  20                  25 agt cgc agg ctg gag aac cgg ctg gtg ctg ctc ttt ggt gct ggg            149
Ser Arg Arg Leu Glu Asn Arg Leu Val Leu Leu Phe Gly Ala Gly
         30                  35                  40 gct tgt cca cag tgc cag gcc ttc gtg ccc atc ctc aag gac ttc ttc        197
Ala Cys Pro Gln Cys Gln Ala Phe Val Pro Ile Leu Lys Asp Phe Phe
         45                  50                  55 gtg cgg ctc aca gat gag ttc tat gta ctg cgg gcg gct cag ctg gcc        245
Val Arg Leu Thr Asp Glu Phe Tyr Val Leu Arg Ala Ala Gln Leu Ala
 60                  65                  70 ctg gtg tac gtg tcc cag gac tcc acg gag gag cag cag gac ctg ttc        293
Leu Val Tyr Val Ser Gln Asp Ser Thr Glu Glu Gln Gln Asp Leu Phe
 75                  80                  85                  90 ctc aag gac atg cca aag aaa tgg ctt ttc ctg ccc ttt gag gat gat        341
Leu Lys Asp Met Pro Lys Lys Trp Leu Phe Leu Pro Phe Glu Asp Asp
             95                 100                 105 ctg agg agg tga                                                        353
Leu Arg Arg <210> SEQ ID NO 6
<211> LENGTH: 109
<212> TYPE: PRT
<213> ORGANISM: Homo sapiens

<400> SEQUENCE: 6
```

```
Met Ala Ser Leu Phe Ser Gly Arg Ile Leu Ile Arg Asn Asn Ser Asp
1               5                   10                  15
Gln Asp Glu Leu Asp Thr Glu Ala Glu Val Ser Arg Arg Leu Glu Asn
            20                  25                  30
Arg Leu Val Leu Leu Phe Phe Gly Ala Gly Ala Cys Pro Gln Cys Gln
        35                  40                  45
Ala Phe Val Pro Ile Leu Lys Asp Phe Phe Val Arg Leu Thr Asp Glu
50                  55                  60
Phe Tyr Val Leu Arg Ala Ala Gln Leu Ala Leu Val Tyr Val Ser Gln
65                  70                  75                  80
Asp Ser Thr Glu Glu Gln Gln Asp Leu Phe Leu Lys Asp Met Pro Lys
                85                  90                  95
Lys Trp Leu Phe Leu Pro Phe Glu Asp Asp Leu Arg Arg
                100                 105
```

<210> SEQ ID NO 7
<211> LENGTH: 686
<212> TYPE: DNA
<213> ORGANISM: Homo sapiens
<220> FEATURE:
<221> NAME/KEY: CDS
<222> LOCATION: (48)..(686)

<400> SEQUENCE: 7

```
ccggggacca cacgccgcgc tgtccccagc acccaaccca ggttacc atg gcc tcc        56
                                                  Met Ala Ser
                                                  1
ctg ttc tct ggc cgc atc ctg atc cgc aac aat agc gac cag gac gag       104
Leu Phe Ser Gly Arg Ile Leu Ile Arg Asn Asn Ser Asp Gln Asp Glu
    5                   10                  15
ctg gat acg gag gct gag gtc agt cgc agg ctg gag aac cgg ctg gtg       152
Leu Asp Thr Glu Ala Glu Val Ser Arg Arg Leu Glu Asn Arg Leu Val
20                  25                  30                  35
ctg ctg ttc ttt ggt gct ggg gct tgt cca cag tgc cag gcc ttc gtg       200
Leu Leu Phe Phe Gly Ala Gly Ala Cys Pro Gln Cys Gln Ala Phe Val
                40                  45                  50
ccc atc ctc aag gac ttc ttc gtg cgg ctc aca gat gag ttc tat gta       248
Pro Ile Leu Lys Asp Phe Phe Val Arg Leu Thr Asp Glu Phe Tyr Val
            55                  60                  65
ctg cgg gcg gct cag ctg gcc ctg gtg tac gtg tcc cag gac tcc acg       296
Leu Arg Ala Ala Gln Leu Ala Leu Val Tyr Val Ser Gln Asp Ser Thr
        70                  75                  80
gag gag cag cag gac ctg ttc ctc aag gac atg cca aag aaa tgg ctt       344
Glu Glu Gln Gln Asp Leu Phe Leu Lys Asp Met Pro Lys Lys Trp Leu
85                  90                  95
ttc ctg ccc ttt gag gat gat ctg agg agg gac ctc ggg cgc cag ttc       392
Phe Leu Pro Phe Glu Asp Asp Leu Arg Arg Asp Leu Gly Arg Gln Phe
100                 105                 110                 115
tca gtg gag cgc ctg ccg gcg gtc gtg gtg ctc aag ccg gac ggg gac       440
Ser Val Glu Arg Leu Pro Ala Val Val Val Leu Lys Pro Asp Gly Asp
                120                 125                 130
gtg ctc act cgc gac ggc gcc gac gag atc cag cgc ctg ggc acc gcc       488
Val Leu Thr Arg Asp Gly Ala Asp Glu Ile Gln Arg Leu Gly Thr Ala
            135                 140                 145
tgc ttc gcc aac tgg cag gag gcg gcc gag gtg ctg gac cgc aac ttc       536
Cys Phe Ala Asn Trp Gln Glu Ala Ala Glu Val Leu Asp Arg Asn Phe
        150                 155                 160
cag ctg cca gag gac ctg gag gac cag gag ccg cgg agc ctc acc gag       584
Gln Leu Pro Glu Asp Leu Glu Asp Gln Glu Pro Arg Ser Leu Thr Glu
165                 170                 175
```

```
tgc ctg cgc cgc cac aag tac cgc gtg gaa aag gcg gcg cga ggc ggg      632
Cys Leu Arg Arg His Lys Tyr Arg Val Glu Lys Ala Ala Arg Gly Gly
180                 185                 190                 195 cgc gac ccc ggg gga ggg ggt ggg gag gag ggc ggg gcc ggg ggg ctg      680
Arg Asp Pro Gly Gly Gly Gly Gly Glu Glu Gly Gly Ala Gly Gly Leu
                200                 205                 210 ttc tga                                                              686
Phe

<210> SEQ ID NO 8
<211> LENGTH: 212
<212> TYPE: PRT
<213> ORGANISM: Homo sapiens

<400> SEQUENCE: 8

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
        35                  40                  45

Ala Phe Val Pro Ile Leu Lys Asp Phe Phe Val Arg Leu Thr Asp Glu
    50                  55                  60

Phe Tyr Val Leu Arg Ala Ala Gln Leu Ala Leu Val Tyr Val Ser Gln
65                  70                  75                  80

Asp Ser Thr Glu Glu Gln Gln Asp Leu Phe Leu Lys Asp Met Pro Lys
                85                  90                  95

Lys Trp Leu Phe Leu Pro Phe Glu Asp Asp Leu Arg Arg Asp Leu Gly
            100                 105                 110

Arg Gln Phe Ser Val Glu Arg Leu Pro Ala Val Val Leu Lys Pro
        115                 120                 125

Asp Gly Asp Val Leu Thr Arg Asp Gly Ala Asp Glu Ile Gln Arg Leu
    130                 135                 140

Gly Thr Ala Cys Phe Ala Asn Trp Gln Glu Ala Ala Glu Val Leu Asp
145                 150                 155                 160

Arg Asn Phe Gln Leu Pro Glu Asp Leu Glu Asp Gln Glu Pro Arg Ser
                165                 170                 175

Leu Thr Glu Cys Leu Arg Arg His Lys Tyr Arg Val Glu Lys Ala Ala
            180                 185                 190

Arg Gly Gly Arg Asp Pro Gly Gly Gly Gly Glu Glu Gly Gly Ala
        195                 200                 205

Gly Gly Leu Phe
    210

<210> SEQ ID NO 9
<211> LENGTH: 600
<212> TYPE: DNA
<213> ORGANISM: Mus musculus
<220> FEATURE:
<221> NAME/KEY: CDS
<222> LOCATION: (265)..(570)

<400> SEQUENCE: 9
ataaaataga gggtgggaga ggttgatggc gtggctctgc ttttttggtgc ggggcacccca     60 gctgtcatcg ctgctgtcgc agcttctgga gtggccactg tgctctctcc tcccttcggc    120
tcaaggtgag ctgttccagc agaaggcggg gctgagaggc gcctagtgct gcgggaggct    180
```

```
cagtgtcatc ttccagctaa caggtggccg tgcagcccag ggctcgtctc tccactgtgt      240
cctcttcacg ccgagctcgt ggcg atg gtg gac gtg ctg ggc ggg cgg cgc        291
                           Met Val Asp Val Leu Gly Gly Arg Arg
                            1               5 ctg gtg acc cgg gag ggc acg gtg gtg gag gcc gag gtg gcg ctg cag       339
Leu Val Thr Arg Glu Gly Thr Val Val Glu Ala Glu Val Ala Leu Gln
 10              15                  20                  25 aac aag gtg gta gct ttg tac ttt gcg gcg ggc cgg tgc tcg ccc agc       387
Asn Lys Val Val Ala Leu Tyr Phe Ala Ala Gly Arg Cys Ser Pro Ser
             30                  35                  40 cgc gac ttc acg ccg ctc ctc tgc gac ttc tac acg gag ctg gtg agc       435
Arg Asp Phe Thr Pro Leu Leu Cys Asp Phe Tyr Thr Glu Leu Val Ser
         45                  50                  55 gag gcg cgg cgg ccc gct ccc ttc gag gtg gtt ttc gtg tcg gca gac       483
Glu Ala Arg Arg Pro Ala Pro Phe Glu Val Val Phe Val Ser Ala Asp
     60                  65                  70 ggc agt gcg gag gag atg ttg gac ttc atg cgc gag ctg cac ggc tcc       531
Gly Ser Ala Glu Glu Met Leu Asp Phe Met Arg Glu Leu His Gly Ser
 75                  80                  85 tgg ctg gca ttg ccc ttc cac gac ccc tac cgg cag tga gtggggaccc        580
Trp Leu Ala Leu Pro Phe His Asp Pro Tyr Arg Gln
 90                  95                 100 aggggtcatg gggctggcgc                                                 600

<210> SEQ ID NO 10
<211> LENGTH: 101
<212> TYPE: PRT
<213> ORGANISM: Mus musculus

<400> SEQUENCE: 10

Met Val Asp Val Leu Gly Gly Arg Arg Leu Val Thr Arg Glu Gly Thr
 1               5                  10                  15

Val Val Glu Ala Glu Val Ala Leu Gln Asn Lys Val Val Ala Leu Tyr
             20                  25                  30

Phe Ala Ala Gly Arg Cys Ser Pro Ser Arg Asp Phe Thr Pro Leu Leu
         35                  40                  45

Cys Asp Phe Tyr Thr Glu Leu Val Ser Glu Ala Arg Arg Pro Ala Pro
     50                  55                  60

Phe Glu Val Val Phe Val Ser Ala Asp Gly Ser Ala Glu Glu Met Leu
 65                  70                  75                  80

Asp Phe Met Arg Glu Leu His Gly Ser Trp Leu Ala Leu Pro Phe His
                 85                  90                  95

Asp Pro Tyr Arg Gln
            100

<210> SEQ ID NO 11
<211> LENGTH: 1164
<212> TYPE: DNA
<213> ORGANISM: Mus musculus
<220> FEATURE:
<221> NAME/KEY: CDS
<222> LOCATION: (300)..(770)

<400> SEQUENCE: 11
ttgactctgg tgggtagaga gggtttgcaa ggcaggataa aatagagggt gggagaggtt      60
gatggcgtgg ctctgctttt tggtgcgggg caccagctgt catcgctgct gtcgcagctt     120
ctggagtggc cactgtgctc tctcctccct tcggctcaag gtgagctgtt ccagcagaag     180
gcggggctga gaggcgccta gtgctgcggg aggctcagtg tcatcttcca gctaacaggt     240
```

```
ggccgtgcag cccagggctc gtctctccac tgtgtcctct tcacgccgag ctcgtggcg      299 atg gtg gac gtg ctg ggc ggg cgg cgc ctg gtg acc cgg gag ggc acg      347
Met Val Asp Val Leu Gly Gly Arg Arg Leu Val Thr Arg Glu Gly Thr
1               5                   10                  15 gtg gtg gag gcc gag gtg gcg ctg cag aac aag gtg gta gct ttg tac      395
Val Val Glu Ala Glu Val Ala Leu Gln Asn Lys Val Val Ala Leu Tyr
                20                  25                  30 ttt gcg gcg ggc cgg tgc tcg ccc agc cgc gac ttc acg ccg ctg ctc      443
Phe Ala Ala Gly Arg Cys Ser Pro Ser Arg Asp Phe Thr Pro Leu Leu
            35                  40                  45 tgc gac ttc tac acg gag ctg gtg agc gag gcg cgg cgg ccc gct ccc      491
Cys Asp Phe Tyr Thr Glu Leu Val Ser Glu Ala Arg Arg Pro Ala Pro
        50                  55                  60 ttc gag gtg gtt ttc gtg tcg gca gac ggc agt gcg gag gag atg ttg      539
Phe Glu Val Val Phe Val Ser Ala Asp Gly Ser Ala Glu Glu Met Leu
65                  70                  75                  80 gac ttc atg cgc gag ctg cac ggc tcc tgg ctg gca ttg ccc ttc cac      587
Asp Phe Met Arg Glu Leu His Gly Ser Trp Leu Ala Leu Pro Phe His
                85                  90                  95 gac ccc tac cgg cat gaa ctg aag aag agg tac gaa atc acc gcc atc      635
Asp Pro Tyr Arg His Glu Leu Lys Lys Arg Tyr Glu Ile Thr Ala Ile
            100                 105                 110 ccc aag ctg gtg gtc atc aag cag aac gga gct gtc atc acc aac aaa      683
Pro Lys Leu Val Val Ile Lys Gln Asn Gly Ala Val Ile Thr Asn Lys
        115                 120                 125 ggg cgg aag cag atc cga gag cgc ggg cta gct tgc ttt cag aac tgg      731
Gly Arg Lys Gln Ile Arg Glu Arg Gly Leu Ala Cys Phe Gln Asn Trp
130                 135                 140 gtg gaa gca gcc gat gtt ttc caa aac ttc tcg ggg tga ccagggcagt      780
Val Glu Ala Ala Asp Val Phe Gln Asn Phe Ser Gly
145                 150                 155 tgctggaagt tcagggcaac tatcttcaaa aagggcttag ctggttccct tctctgctga   840
ggaatgtcat tgtagagtca ccatgctgtg acagagagca taaactgctc aggaaagaac   900
tacgtctgcc cctgtgggt cctagagctc cgttgaatgt ttatttctta cacctttctc    960
caccggtgcc taggatccag gacacatcag ccacgagtta acagaactct atgcaagatg   1020
ctctttccta caggaaattt ctttgataaa ttgacctatg gaggtgatac attttctgat   1080
gacatttttg tgatgctttg gtaaacgtat ttattactcg ggtttgtaga ctgtgtaatt   1140
taataaacca acactcacac tttg                                          1164
```

<210> SEQ ID NO 12
<211> LENGTH: 156
<212> TYPE: PRT
<213> ORGANISM: Mus musculus

<400> SEQUENCE: 12

```
Met Val Asp Val Leu Gly Gly Arg Arg Leu Val Thr Arg Glu Gly Thr
1               5                   10                  15

Val Val Glu Ala Glu Val Ala Leu Gln Asn Lys Val Val Ala Leu Tyr
                20                  25                  30

Phe Ala Ala Gly Arg Cys Ser Pro Ser Arg Asp Phe Thr Pro Leu Leu
            35                  40                  45

Cys Asp Phe Tyr Thr Glu Leu Val Ser Glu Ala Arg Arg Pro Ala Pro
        50                  55                  60

Phe Glu Val Val Phe Val Ser Ala Asp Gly Ser Ala Glu Glu Met Leu
65                  70                  75                  80
```

```
Asp Phe Met Arg Glu Leu His Gly Ser Trp Leu Ala Leu Pro Phe His
            85                  90                  95

Asp Pro Tyr Arg His Glu Leu Lys Lys Arg Tyr Glu Ile Thr Ala Ile
        100                 105                 110

Pro Lys Leu Val Val Ile Lys Gln Asn Gly Ala Val Ile Thr Asn Lys
    115                 120                 125

Gly Arg Lys Gln Ile Arg Glu Arg Gly Leu Ala Cys Phe Gln Asn Trp
130                 135                 140

Val Glu Ala Ala Asp Val Phe Gln Asn Phe Ser Gly
145                 150                 155

<210> SEQ ID NO 13
<211> LENGTH: 1472
<212> TYPE: DNA
<213> ORGANISM: Homo sapiens
<220> FEATURE:
<221> NAME/KEY: CDS
<222> LOCATION: (331)..(738)

<400> SEQUENCE: 13
```

| | |
|---|---:|
| gtgtgggcgg ggcgcagttg ggggagggtg cagagacctg agggcttgag gttgcctggc | 60 |
| tggccccgct cccagaggcg ggtgccgcgc tgtcgcccag gtatctgggg tctctggtgt | 120 |
| ctgagtgtct cattgtcggc gcgaacacaa ttgctccagc cacaggcgag gcctggccaa | 180 |
| ggtgtgggcg catctagggc aggtcttgag aggtccagcg cccgtggtg cggacagagg | 240 |
| cggggcaccg cggcgctcgc cgccgcctcc ccgcaggtga tcatcctcct gcaggtgtcc | 300 |

```
tcgggtctca ggtggctgcg tgtctgcgcc atg gtt gac att ctg ggc gag cgg        354
                                Met Val Asp Ile Leu Gly Glu Arg
                                  1               5 cac ctg gtg acc tgt aag ggc gcg acg gtg gag gcc gag gcg gcg ctg        402
His Leu Val Thr Cys Lys Gly Ala Thr Val Glu Ala Glu Ala Ala Leu
         10                  15                  20 cag aac aag gtg gtg gca ctg tac ttc gcg gcg gcc cgg tgc gcg ccg        450
Gln Asn Lys Val Val Ala Leu Tyr Phe Ala Ala Ala Arg Cys Ala Pro
 25                  30                  35                  40 agc cgc gac ttc acg ccg ctg ctc tgc gac ttc tat acg gcg ctg gtg        498
Ser Arg Asp Phe Thr Pro Leu Leu Cys Asp Phe Tyr Thr Ala Leu Val
                 45                  50                  55 gcc gag gcg cgg cgg ccc gcg ccc ttc gaa gtg gtc ttc gtg tca gcc        546
Ala Glu Ala Arg Arg Pro Ala Pro Phe Glu Val Val Phe Val Ser Ala
             60                  65                  70 gac ggc agc tgc cag gag atg ctg gac ttc atg cgc gag ctg cat ggc        594
Asp Gly Ser Cys Gln Glu Met Leu Asp Phe Met Arg Glu Leu His Gly
         75                  80                  85 gcc tgg ctg gcg ctg ccc ttc cac gac ccc tac cgg caa cgg agt ctc        642
Ala Trp Leu Ala Leu Pro Phe His Asp Pro Tyr Arg Gln Arg Ser Leu
 90                  95                 100 gct ctg ttg ccc agg ctg gag tgc agt ggc gtg atc tta gct cac tgc        690
Ala Leu Leu Pro Arg Leu Glu Cys Ser Gly Val Ile Leu Ala His Cys
105                 110                 115                 120 aac ctt tgc ctc ctg ggt tca agt gat tct cta gcc tta gcc tcc tga        738
Asn Leu Cys Leu Leu Gly Ser Ser Asp Ser Leu Ala Leu Ala Ser
                125                 130                 135
```

| | |
|---|---:|
| gcatctggga ctacagccat tgctgtgaat tacgtgaggg aaagatattg aagaggagtt | 798 |
| ggacactccg agagtgcagc tgttctcccc ccgcaccatc cgtgtcctgc attctgcgag | 858 |
| tctgtgctca ttaacaatgt gctgtgacca tgtgactcag caatcctgct gctgggtata | 918 |

| | |
|---|---|
| tacccgaaag aaaggaaaag gaagccagta tattgaagag gtatctgcac ccccatgttt | 978 |
| attgcagcac tgttcacaac agccaagatt tggaagcaac ctaagtgtcc atcaacagat | 1038 |
| gaatggataa agaaaacgtg gtacatatac acaatggagt actcttcagc cattaaaaaa | 1098 |
| atgagattct gtcatttgca ataatataga tggaaaagga ggcccttatg tgaagtgaaa | 1158 |
| taagccaggc acagaaagac aaacatcaca tgttctcact tatttgtggg atctaatgat | 1218 |
| caaaacaatt gaactcttgg acatagagag tagaaggttg gttaccagaa gctgaaaagg | 1278 |
| aaagtggggt tgggaggaag gtgggaatgg ttaataggta caaaaaaata caagaataa | 1338 |
| ataagaccta atatttgata gcacaacagt gtgactactg tcaataatca tttaattgta | 1398 |
| catttaaaaa taactataat tgcattgttt gtaacacaaa agataaatgc ttgaggagaa | 1458 |
| aaaaaaaaaa aaaa | 1472 |

<210> SEQ ID NO 14
<211> LENGTH: 135
<212> TYPE: PRT
<213> ORGANISM: Homo sapiens

<400> SEQUENCE: 14

```
Met Val Asp Ile Leu Gly Glu Arg His Leu Val Thr Cys Lys Gly Ala
1               5                   10                  15

Thr Val Glu Ala Glu Ala Ala Leu Gln Asn Lys Val Val Ala Leu Tyr
            20                  25                  30

Phe Ala Ala Ala Arg Cys Ala Pro Ser Arg Asp Phe Thr Pro Leu Leu
        35                  40                  45

Cys Asp Phe Tyr Thr Ala Leu Val Ala Glu Ala Arg Arg Pro Ala Pro
    50                  55                  60

Phe Glu Val Val Phe Val Ser Ala Asp Gly Ser Cys Gln Glu Met Leu
65                  70                  75                  80

Asp Phe Met Arg Glu Leu His Gly Ala Trp Leu Ala Leu Pro Phe His
                85                  90                  95

Asp Pro Tyr Arg Gln Arg Ser Leu Ala Leu Leu Pro Arg Leu Glu Cys
            100                 105                 110

Ser Gly Val Ile Leu Ala His Cys Asn Leu Cys Leu Leu Gly Ser Ser
        115                 120                 125

Asp Ser Leu Ala Leu Ala Ser
    130                 135
```

<210> SEQ ID NO 15
<211> LENGTH: 702
<212> TYPE: DNA
<213> ORGANISM: Mus musculus

<400> SEQUENCE: 15

| | |
|---|---|
| atcggatcct ctctgggtcc ccagctcctt gcatactgct accatggcat ctctcttctc | 60 |
| tggacgcatc ttgatcagga acaacagcga ccaggatgaa gtggagacag aggcagagct | 120 |
| gagccgtagg ttagagaatc gtctggtgtt gctgttcttc ggcgccggcg cctgtcccca | 180 |
| gtgccaggcc ttgccccagt cctcaaagac ttcttcgtgc ggctcactga cgagttctac | 240 |
| gtgctgcggg cagcacagct ggccctggtc tatgtgtccc aggacctac agaggagcaa | 300 |
| caggacctct tcctcaggga catgcctgaa aaatggctct tcctgccgtc ccactgatga | 360 |
| actgaggagg tgaggcccca gggaagacca gggagggctt cctggagaag gcatttccct | 420 |
| ggaggtttac tgtcctggta ctacttgtgc actaaagagg tattcctcca caccaaccac | 480 |

-continued

```
aggcgacaac aacacacaag aggtgtccca tccgctcttc catcacagcc cactgacgcc    540
agacagcatc gcgacgctca cggctcagaa aaacacaggt agtctcacag gcctgccatc    600
ctaatactgg ccaccctgag cacaagagcg atggctacaa gcctcaaggc tagaatctaa    660
aaccacgagg tggggaccgt aggcccact ccccgggagc gc                        702
```

<210> SEQ ID NO 16
<211> LENGTH: 387
<212> TYPE: DNA
<213> ORGANISM: Rattus norvegicus

<400> SEQUENCE: 16

```
cggccgctta attaagacgg atccccgact acgtagtcgg gaattcggca cgaggggccg    60
catcttgatc aggaacaaca gcgaccagga tgaagtggag acagaggcag agctgagccg   120
ccggttagag aatcgtcttg tgctactgtt cttcggtgct ggggcctgtc cccagtgcca   180
ggccttcgcc ccagtcctca aagacttctt cgtgcggctc actgatgagt tctacgtgct   240
acgggcagca cagctggccc tggtctatgt gtcccaggac cctacagagg agcaacagga   300
cctgttcctc cgggacatgc ctgaaaagtg gctcttcctg ccgttccatg atgacctgag   360
gagagacctc gggcgccagt tctccgt                                        387
```

<210> SEQ ID NO 17
<211> LENGTH: 759
<212> TYPE: DNA
<213> ORGANISM: Mus musculus

<400> SEQUENCE: 17

```
cagctccttg catactgcta ccatggcatc tctcttctct ggacgcatct tgatcaggaa    60
caacagcgac caggatgaag tggagacaga ggcagagctg agccgtaggt tagagaatcg   120
tctggtgtgc tgttcttcgg cgccggcgcc tgtccccagt gccaggcctt gccccagtcc   180
tcaaagactt cttcgtgcgg ctcactgacg agttctacgt gctgcgggca gcacagctgg   240
ccctggtcta tgtgtcccag gaccctacag aggagcaaca ggacctcttc ctcagggaca   300
tgcctgaaaa atggctcttc ctgccgttcc atgatgaact gaggagggac ctcgggcgcc   360
agttctctgt ccgtcaactg ccagcggttg tggtacttaa gcctggtggg acgtgctga    420 caagcgacgc cacggaggag atccagcgtc tgggacccgc ctgctttgcc aactggcagg   480
aggccgcaga gctcctggac cgcagcttcc tgcaaccgga ggatttggat gagcctgcgc   540
ggcgcagcat caccgagcct ctgcgccgtc gcaagtaccg agtagaccgg gatgtcggcg   600 ggagcgggc gaaacggcgc gactctggtg aaccccaggg ggacgcgggt acaagggcgg   660
agctctggtg actcccaggg taggagtggg gaccggagct ctggtgacac caaagtaccg   720
gtgcacgacc gaggttgatg accctcccga aggaaccgg                          759
```

<210> SEQ ID NO 18
<211> LENGTH: 443
<212> TYPE: DNA
<213> ORGANISM: Rattus norvegicus
<220> FEATURE:
<221> NAME/KEY: modified_base
<222> LOCATION: (46)..(46)
<223> OTHER INFORMATION: a, c, t, g, unknown or other

<400> SEQUENCE: 18

```
acgaggtcaa ccttggctac acagggagtc tgaggacagc atgggntaca agaaaccctc    60
tctcaaaacc aaacaaggcc tggcagtact agtgcacttg ggaggcagag gaacaacagc   120
```

```
gaccaggatg aagtggagac agaggcagag ctgagccgcc ggttagagaa tcgtcttgtg    180
ctactgttct tcggtgctgg ggcctgtccc cagtgccagg ccttcgcccc agtcctcaaa    240
gacttcttcg tgcggctcac tgatgagttc tacgtgctac gggcagcaca gctggccctg    300
gtctatgtgt cccaggaccc tacagaggag caacaggacc tgttcctccg ggacatgcct    360
gaaaagtggc tcttcctgcc gttccatgat gacctgagga gtaataaaaa ttagaggttg    420
tggctcaaaa aaaaaaaaaa aaa                                            443

<210> SEQ ID NO 19
<211> LENGTH: 889
<212> TYPE: DNA
<213> ORGANISM: Homo sapiens

<400> SEQUENCE: 19
acgccgcgct gtccccagca cccaacccag gttaccatgg cctccctgtt ctctggccgc     60
atcctgatcc gcaacaatag cgaccaggac gagctggata cggaggctga ggtcagtcgc    120
aggctggaga accggctggt gctgctgttc tttggtgctg gggcttgtcc acagtgccag    180
gccttcgtgc ccatcctcaa ggacttcttc gtgcggctca cagatgagtt ctatgtactg    240
cgggcggctc agctggccct ggtgtacgtg tcccaggact ccacggagga gcagcaggac    300
ctgttcctca aggacatgcc aaagaaatgg cttttcctgc cctttgagga tgatctgagg    360
agggacctcg ggcgccagtt ctcagtggag cgcctgccgg cggtcgtggt gctcaagccg    420
gacggggacg tgctcactcg cgacggcgcc gacgagatcc agcgcctggg caccgcctgc    480
ttcgccaact ggcaggaggc ggccgaggtg ctggaccgca acttccagct gccagaggac    540
ctggaggacc aggagccacg gagcctcacc gagtgcctgc gccgccacaa gtaccgcgtg    600
gaaaaggcgg cgcgaggcgg cgcgacccgg gggaggggct ggggacggag gccggggccc    660 gggggggctgt actgaccgct gggtggagca gaggagggg gattggtgga agaacaacaa    720
ccacacgcag ccagcaccag gtatcccgac taggggagac agggcgaaga cctgacccaa    780
agcacaacca ccggggacac taaacgactc aactcaatcc tgtgggcacc aggacaccgc    840
aaaaaaaaac aaaaaaagca aaatgcaaaa aaagacagga catacgacg              889

<210> SEQ ID NO 20
<211> LENGTH: 348
<212> TYPE: DNA
<213> ORGANISM: Homo sapiens

<400> SEQUENCE: 20
tgtcctcggg tctcaggtgg ctgcgtgtct gcgccatggt tgacattctg ggcgagcggc     60
acctggtgac ctgtaagggc gcgacggtgg aggccgaggc ggcgctgcag aacaaggtgg    120
tggcactgta cttcgcggcg gcccggtgcg cgccgagccg cgacttcacg ccgctgctct    180
gcgacttcta tacggcgctg gtggccgagg cgcggcggcc cgcgcccttc gaagtggtct    240
tcgtgtcagc cgacggcagc tcccaggaga tgctggactt catgcgcgag ctgcatggcg    300
cctggctggc gctgcccttc cacgaccct accggcacca ttgctgtg                 348

<210> SEQ ID NO 21
<211> LENGTH: 340
<212> TYPE: DNA
<213> ORGANISM: Homo sapiens

<400> SEQUENCE: 21
```

```
tgtcctcggg tctcaggtgg ctgcgtgtct gcgccatggt tgacattctg ggcgagcggc      60
acctggtgac ctgtaagggc gcgacggtgg aggccgaggc ggcgctgcag aacaaggtgg     120
tggcactgta cttcgcggcg gccggtgcgc gccgagccgc gattcacgcc gctgctctgc    180
gacttctata cggcgctggt ggccgagcgc ggggccgcgc cttcgaagtg gtcttcgtgt    240
cagccgacgg cagctcccag gagatgctgg acttcatgcg cgagctgatg gcgcctggct    300
ggcgctgcct ccacgaccc ctaccggcac agccggagcc                           340
```

```
<210> SEQ ID NO 22
<211> LENGTH: 348
<212> TYPE: DNA
<213> ORGANISM: Homo sapiens

<400> SEQUENCE: 22
```

```
tgtcctcggg tctcaggtgg ctgcgtgtct gcgccatggt tgacattctg ggcgagcggc      60
acctggtgac ctgtaagggc gcgacggtgg aggccgaggc ggcgctgcag aacaaggtgg     120
tggcactgta cttcgcggcg gcccggtgcg cgccgagccg cgacttcacg ccgctgctct    180
gcgacttcta tacggcgctg gtggccgagg cgcggcggcc cgcgcccttc gaagtggtct    240
tcgtgtcagc cgacggcagc tgccaggaga tgctggactt catgcgcgag ctgcatggcg    300
cctggctggc gctgcccttc acgaaccct accggcaacg gagtctcg                  348
```

```
<210> SEQ ID NO 23
<211> LENGTH: 350
<212> TYPE: DNA
<213> ORGANISM: Homo sapiens

<400> SEQUENCE: 23
```

```
tgtcctcggg tctcaggtgg ctgcgtgtct gcgccatggt tgacattctg ggcgagcggc      60
acctggtgac ctgtaagggc gcgacggtgg aggccgaggc ggcgctgcag aacaaggtgg     120
tggcactgta cttcgcggcg gcccggtgcg cgccgagccg cgacttcacg ccgctgctct    180
gcgacttcta tacggcgctg gtggccgagg cgcggcggcc cgcgcccttc gaagtggtct    240
tcgtgtcagc cgacggcagc tgccaggaga tgcttggact tcatgcgcga gctgcattgc    300
gcctggcttg cgctgccct ccacgaccc ctaccggcaa cggagtctcg                 350
```

```
<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tctatgtgtc ccaggaccct acag                                            24
```

```
<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tttatgcaca agtagtacca ggacag                                          26
```

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
cgggatccat ggcatctctc ttctctggac gc            32

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ggaattctca cctcctcagt tcatcatgga a            31

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
tgttaccaat ctgaagtggg agcggccgac aatttttttt ttttttttt            50

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
aattcggcac gagg            14

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
cctcgtgccg            10

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gtaatacgac tcactatagg gc            22

<210> SEQ ID NO 32

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctattacgtc aagcctgtag cc                                               22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
catcctcatc tttcttccct tc                                               22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gccagcgttt tctgcctttt ac                                               22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aagccctgcc tgctctaaca tc                                               22

<210> SEQ ID NO 36
<211> LENGTH: 119
<212> TYPE: PRT
<213> ORGANISM: Homo sapiens

<400> SEQUENCE: 36

Met Val Asp Ile Leu Gly Glu Arg His Leu Val Thr Cys Lys Gly Ala
1               5                   10                  15

Thr Val Glu Ala Glu Ala Ala Leu Gln Asn Lys Val Val Ala Leu Tyr
            20                  25                  30

Phe Ala Ala Ala Arg Cys Ala Pro Ser Arg Asp Phe Thr Pro Leu Leu
        35                  40                  45

Cys Asp Phe Tyr Thr Ala Leu Val Ala Glu Ala Arg Arg Pro Ala Pro
    50                  55                  60

Phe Glu Val Val Phe Val Ser Ala Asp Gly Ser Cys Gln Glu Met Leu
65                  70                  75                  80

Asp Phe Met Arg Glu Leu His Gly Ala Trp Leu Ala Leu Pro Phe His
                85                  90                  95

Glu Pro Tyr Arg Gln Arg Ser Leu Ala Leu Leu Pro Arg Leu Glu Cys
            100                 105                 110
```

Ser Gly Val Ile Leu Ala His
    115

<210> SEQ ID NO 37
<211> LENGTH: 306
<212> TYPE: DNA
<213> ORGANISM: Mus musculus

<400> SEQUENCE: 37

| | | | | | |
|---|---|---|---|---|---|
| atggtggacg | tgctgggcgg | gcggcgcctg | gtgacccggg | agggcacggt | ggtggaggcc | 60 |
| gaggtggcgc | tgcagaacaa | ggtggtagct | ttgtactttg | cggcgggccg | gtgctcgccc | 120 |
| agccgcgact | tcacgccgct | gctctgcgac | ttctacacgg | agctggtgag | cgaggcgcgg | 180 |
| cggcccgctc | ccttcgaggt | ggttttcgtg | tcggcagacg | gcagtgcgga | ggagatgttg | 240 |
| gacttcatgc | gcgagctgca | cggctcctgg | ctggcattgc | ccttccacga | cccctaccgg | 300 |
| cagtga | | | | | | 306 |

<210> SEQ ID NO 38
<211> LENGTH: 330
<212> TYPE: DNA
<213> ORGANISM: Mus musculus

<400> SEQUENCE: 38

| | | | | | |
|---|---|---|---|---|---|
| atggcatctc | tcttctctgg | acgcatcttg | atcaggaaca | acagcgacca | ggatgaagtg | 60 |
| gagacagagg | cagagctgag | ccgtaggtta | gagaatcgtc | tggtgttgct | gttcttcggc | 120 |
| gccggcgcct | gtccccagtg | ccaggccttt | gccccagtcc | tcaaagactt | cttcgtgcgg | 180 |
| ctcactgacg | agttctacgt | gctgcgggca | gcacagctgg | ccctggtcta | tgtgtcccag | 240 |
| gaccctacag | aggagcaaca | ggacctcttc | ctcagggaca | tgcctgaaaa | atggctcttc | 300 |
| ctgccgttcc | atgatgaact | gaggaggtga | | | | 330 |